United States Patent
Swager et al.

(10) Patent No.: US 9,459,222 B2
(45) Date of Patent: Oct. 4, 2016

(54) METHODS FOR DEPOSITION OF MATERIALS INCLUDING MECHANICAL ABRASION

(71) Applicant: Massachusetts Institute of Technology, Cambridge, MA (US)

(72) Inventors: Timothy M. Swager, Newton, MA (US); Katherine A. Mirica, Waltham, MA (US); Joseph M. Azzarelli, Cambridge, MA (US); Jonathan G. Weis, Somerville, MA (US); Jan Schnorr, Cambridge, MA (US); Birgit Esser, Bonn (DE)

(73) Assignee: Massachusetts Institute of Technology, Cambridge, MA (US)

( * ) Notice: Subject to any disclaimer, the term of this patent is extended or adjusted under 35 U.S.C. 154(b) by 70 days.

(21) Appl. No.: 13/800,169

(22) Filed: Mar. 13, 2013

(65) Prior Publication Data

US 2013/0330231 A1    Dec. 12, 2013

Related U.S. Application Data

(60) Provisional application No. 61/621,116, filed on Apr. 6, 2012.

(51) Int. Cl.
  *G01N 27/00* (2006.01)
  *G01N 27/04* (2006.01)
  *G01N 27/07* (2006.01)
  *G01N 27/12* (2006.01)

(52) U.S. Cl.
  CPC .......... *G01N 27/12* (2013.01); *Y10T 29/49002* (2015.01)

(58) Field of Classification Search
  CPC .................. Y10T 29/49002; G01N 27/12
  USPC .................................. 977/700–706
  See application file for complete search history.

(56) References Cited

U.S. PATENT DOCUMENTS 3,834,910 A * 9/1974 Mukai et al. .............. 523/164
4,889,961 A * 12/1989 Carlson ..................... 174/261
6,797,428 B1 9/2004 Skotheim et al.
(Continued)

FOREIGN PATENT DOCUMENTS

WO   WO 2008/089787 A1   7/2008
WO   WO 2011/055039 A1 * 5/2011

OTHER PUBLICATIONS

Lobez, Jose M., and Timothy M. Swager. "Radiation Detection: Resistivity Responses in Functional Poly (Olefin Sulfone)/Carbon Nanotube Composites." (2009).*

(Continued)

*Primary Examiner* — Lyle Alexander
*Assistant Examiner* — Robert Eom
(74) *Attorney, Agent, or Firm* — Wolf, Greenfield & Sacks, P.C.

(57) ABSTRACT

Methods described herein may be useful in the fabrication and/or screening of devices (e.g., sensors, circuits, etc.) including conductive materials. In some embodiments, a conductive material is formed on a substrate using mechanical abrasion. The methods described herein may be useful in fabricating sensors, circuits, tags for remotely-monitored sensors or human/object labeling and tracking, among other devices. In some cases, devices for determining analytes are also provided.

30 Claims, 23 Drawing Sheets

(56) References Cited

U.S. PATENT DOCUMENTS

2008/0035481 A1* 2/2008 McCormack .......... B82Y 15/00
204/433
2011/0089051 A1 4/2011 Wang et al.

OTHER PUBLICATIONS

Li, Jing, et al. "Carbon nanotube sensors for gas and organic vapor detection." Nano Letters 3.7 (2003): 929-933.*
International Search Report and Written Opinion for Application No. PCT/US2013/030846 mailed Nov. 8, 2013.
Albrecht et al., Ultrahigh-vacuum scanning tunneling microscopy and spectroscopy of single-walled carbon nanotubes on hydrogen-passivated Si(100) surfaces. Appl Phys Lett. Dec. 15, 2003;83(24):5029-31.
Alvarez et al., Abrasion as a catalyst deposition technique for carbon nanotube growth. J Am Chem Soc. Oct. 21, 2009;131(41):15041-8.
Ammu et al., Flexible, all-organic chemiresistor for detecting chemically aggressive vapors. J Am Chem Soc. Mar. 14, 2012;134(10):4553-6. Epub Mar. 1, 2012.
Bahr et al., Covalent chemistry of single-walled carbon nanotubes. Journal of Mater Chem. 2002;12:1952-8.
Barr et al., Direct monolithic integration of organic photovoltaic circuits on unmodified paper. Adv Mater. Aug. 16, 2011;23(31):3500-3505. Epub Jul. 8, 2011.
Bekyarova et al., Chemically functionalized single-walled carbon nanotubes as ammonia sensors. J Phys Chem B. 2004;108(51):19717-20.
Britz et al., Noncovalent interactions of molecules with single walled carbon nanotubes. Chem Soc Rev. Jul. 2006;35(7):637-59. Epub Mar. 23, 2006.
Esser et al., Selective detection of ethylene gas using carbon nanotube-based devices: utility in determination of fruit ripeness. Angew Chem Int Ed Engl. Jun. 4, 2012;51(23):5752-6. Epub Apr. 19, 2012.
Kauffman et al., Carbon nanotube gas and vapor sensors. Angew Chem Int Ed Engl. 2008;47(35):6550-70.
Kong et al., Nanotube molecular wires as chemical sensors. Science. Jan. 28, 2000;287(5453):622-5.
Li et al., Carbon nanotube sensors for gas and organic vapor detection. Nano Letters. Jun. 13, 2003;3(7):929-33.
Martinez et al., Diagnostics for the developing world: microfluidic paper-based analytical devices. Anal Chem. Jan. 1, 2010;82(1):3-10.
Martinez et al., Patterned paper as a platform for inexpensive, low-volume, portable bioassays. Angew Chem Int Ed Engl. Feb. 12, 2007;46(8):1318-20.
Mirica et al., Mechanical drawing of gas sensors on paper. Angew Chem Int Ed Engl. Oct. 22, 2012;51(43):10740-5. Epub Oct. 4, 2012.
Nie et al., Electrochemical sensing in paper-based microfluidic devices. Lab Chip. Feb. 21, 2010;10(4):477-83. Epub Dec. 3, 2009.
Potyrailo et al., Materials and transducers toward selective wireless gas sensing. Chem Rev. Nov. 9, 2011;111(11):7315-54. Epub Sep. 7, 2011.
Röck et al., Electronic nose: current status and future trends. Chem Rev. Feb. 2008;108(2):705-25. Epub Jan. 19, 2008.
Schnorr et al., Emerging applications of carbon nanotubes. Chem Mater. 2011;23:646-57.
Siegel et al., Foldable printed circuit boards on paper substrates. Adv Funct Mater. Jan. 8, 2010;20(1):28-35.
Stitzel et al., Artificial noses. Annu Rev Biomed Eng. Aug. 15, 2011;13:1-25.
Thom et al., "Fluidic batteries" as low-cost sources of power in paper-based microfluidic devices. Lab Chip. Apr. 24, 2012;12(10):1768-70. Epub Mar. 26, 2012.
Tobjörk et al., Paper electronics. Adv Mater. May 3, 2011;23(17):1935-61. Epub Mar. 23, 2011.
Vyas et al., Inkjet printed, self powered, wireless sensors for environmental, gas, and authentication-base sensing. IEEE Sens J. 2011;11(12):3139-52.
Wang et al., Carbon nanotube/polythiophene chemiresistive sensors for chemical warfare agents. J Am Chem Soc. Apr. 23, 2008;130(16):5392-3. Epub Mar. 29, 2008.
Wang et al., Molecular recognition for high selectivity in carbon nanotube/polythiophene chemiresistors. Angew Chem Int Ed Engl. 2008;47(44):8394-6.
Wang et al., Paper-based three-dimensional electrochemical immunodevice based on multi-walled carbon nanotubes functionalized paper for sensitive point-of-care testing. Biosens Bioelectron. Feb. 15, 2012;32(1):238-43. Epub Dec. 23, 2011.
Wang et al., Simple, rapid, sensitive, and versatile SWNT-paper sensor for environmental toxin detection competitive with ELISA. Nano Lett. Dec. 2009;9(12):4147-52.
Wilson et al., Applications and advances in electronic-nose technologies. Sensors (Basel). 2009;9(7):5099-148. Epub Jun. 29, 2009.
Zhang et al., Modular functionalization of carbon nanotubes and fullerenes. J Am Chem Soc. Jun. 24, 2009;131(24):8446-54.
Zhang et al., Poly(m-aminobenzene sulfonic acid) functionalized single-walled carbon nanotubes based gas sensor. Nanotechnology. Mar. 23, 2007;18(16):156604. 6 pages.

* cited by examiner

US 9,459,222 B2

METHODS FOR DEPOSITION OF MATERIALS INCLUDING MECHANICAL ABRASION

RELATED APPLICATIONS

This application claims priority under 35 U.S.C. §119(e) to U.S. Provisional Application Ser. No. 61/621,116, filed Apr. 6, 2012, the contents of which are incorporated herein by reference in its entirety for all purposes.

STATEMENT REGARDING FEDERALLY SPONSORED RESEARCH OR DEVELOPMENT

This invention was made with government support under Grant No. W911NF-07-D-0004 awarded by the Army Research Office. The government has certain rights in this invention.

FIELD OF THE INVENTION

Devices comprising conductive materials are described, and related methods.

BACKGROUND OF THE INVENTION

Development of simple and low-cost technologies for detecting and identifying gases and volatile organic compounds (VOCs) is important for improving human health, safety, and quality of life. Nanostructured forms of carbon, such as carbon nanotubes and graphene, represent an emerging class of materials in chemical sensing. A useful feature of these materials is that their electrical conductance is extremely sensitive to changes in local chemical environment and can be altered by several mechanisms, such as transfer of charge, annealing, and swelling. Dependence on expensive specialized equipment for the fabrication of devices, the need for solution processing, and requirements for chemical functionalization for achieving specificity, however, have limited the applications and wide applicability of these materials. For example, carbon nanotubes (CNTs) are promising materials for sensing of gases and volatile organic compounds; however, their poor solubility in most solvents has hindered the solution-based process of covalent or non-covalent chemical functionalization of CNTs, and the subsequent integration of these materials into devices.

Additionally, methods for fabricating devices with CNTs are often expensive and time-consuming. For example, covalent and non-covalent functionalization of CNTs to generate selective sensing materials in solution often takes hours and sometimes days. Integration of these materials into devices by drop casting, spin coating, and inkjet printing typically requires prolonged drying times to remove solvent, and often involves several repeated processing cycles to obtain devices with desired electrical properties. Furthermore, known methods for fabricating such devices often require the use of toxic solvents, surfactants, or prolonged sonication for dispersing materials in solution.

SUMMARY OF THE INVENTION

Devices, methods for fabricating devices, and methods for determining analytes, are provided.

In some embodiments, methods for fabricating devices are provided. In some embodiments, the method involves providing an article comprising a conductive material; contacting the article with a surface of a substrate via mechanical abrasion, thereby forming the conductive material on the surface of the substrate; providing an electrode material in electrochemical communication with the conductive material; and applying a potential to the electrode material.

In some embodiments, the method involves providing an article comprising a conductive material, wherein the article is in solid form; contacting the article in solid form with a surface of a substrate and in the absence of a solvent, thereby forming the conductive material on the surface of the substrate; providing an electrode material in electrochemical communication with the conductive material; and applying a potential to the electrode material.

In some embodiments, the method involves providing an article comprising a conductive material, wherein the article is in solid form; contacting the article in solid form with a surface of a substrate and in the absence of a solvent, thereby forming the conductive material on the surface of the substrate; and forming an electrical circuit comprising the conductive material.

In some embodiments, devices for determining an analyte are provided. In some cases, the device comprises a first electrode and a second electrode; a sensor material in electrochemical communication with the first and the second electrodes, wherein resistance to current flow between the first and second electrode is affected by the sensor material, wherein the sensor material comprises a conductive material and a fluorine-containing aromatic species integrally connected to at least a portion of the conductive material, and wherein the analyte, if present, interacts with the sensor material to affect resistance to current flow between the first and second electrodes, thereby generating a signal in the device by which the analyte is determined.

In some cases, the device comprises a first electrode and a second electrode; a sensor material in electrochemical communication with the first and the second electrodes, wherein resistance to current flow between the first and second electrode is affected by the sensor material, wherein the sensor material comprises a conductive material and a copper-containing species integrally connected to at least a portion of the conductive material, and wherein the analyte, if present, interacts with the sensor material to affect resistance to current flow between the first and second electrodes, thereby generating a signal in the device by which the analyte is determined.

In some cases, the device comprises a first electrode and a second electrode; a sensor material in electrochemical communication with the first and the second electrodes, wherein resistance to current flow between the first and second electrode is affected by the sensor material, wherein the sensor material comprises a conductive material and a palladium-containing species integrally connected to at least a portion of the conductive material, and wherein the analyte, if present, interacts with the sensor material to affect resistance to current flow between the first and second electrodes, thereby generating a signal in the device by which the analyte is determined.

In some cases, the device comprises a first electrode and a second electrode; a sensor material in electrochemical communication with the first and the second electrodes, wherein resistance to current flow between the first and second electrode is affected by the sensor material, wherein the sensor material comprises a conductive material and a species comprising a fluorinated alcohol group integrally connected to at least a portion of the conductive material, and wherein the analyte, if present, interacts with the sensor material to affect resistance to current flow between the first and second electrodes, thereby generating a signal in the device by which the analyte is determined.

In some embodiments, the device comprises a first electrode and a second electrode; a sensor material in electrochemical communication with the first and the second electrodes, wherein resistance to current flow between the first and second electrode is affected by the sensor material, wherein the sensor material comprises a conductive material and a species integrally connected to at least a portion of the conductive material, and wherein the analyte, if present, interacts with the sensor material to affect resistance to current flow between the first and second electrodes, thereby generating a signal in the device by which the analyte is determined, wherein the species is

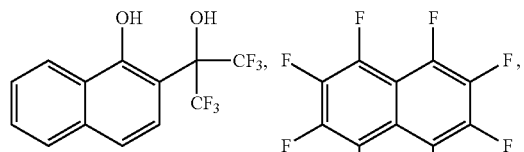

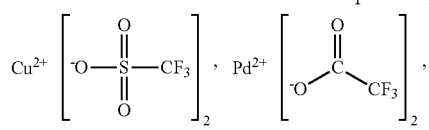

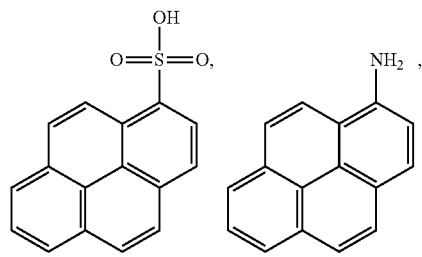

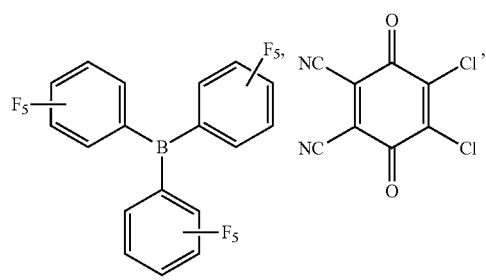

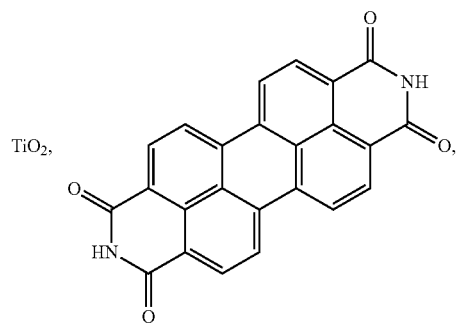

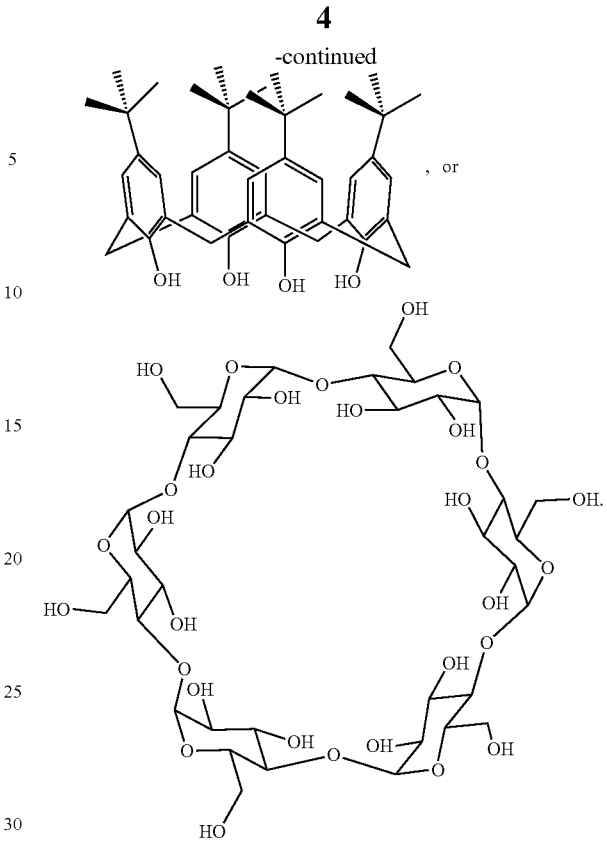

In any of the devices described herein, the conductive material and species, if present, may be formed via mechanical abrasion of an article comprising the conductive material and species, if present, on the surface of a substrate.

Methods for determining analytes are also provided. Any of the devices disclosed herein may be utilized in a method for determining an analyte. In some embodiments, the method may comprise providing a device capable of producing a first, determinable signal in the absence of an analyte; exposing the device to a sample suspected of containing an analyte, wherein the analyte, if present, may interact with one or more components of the device to cause a change in the signal produced by the device; and determining the change in signal, thereby determining the analyte.

Figure 1:
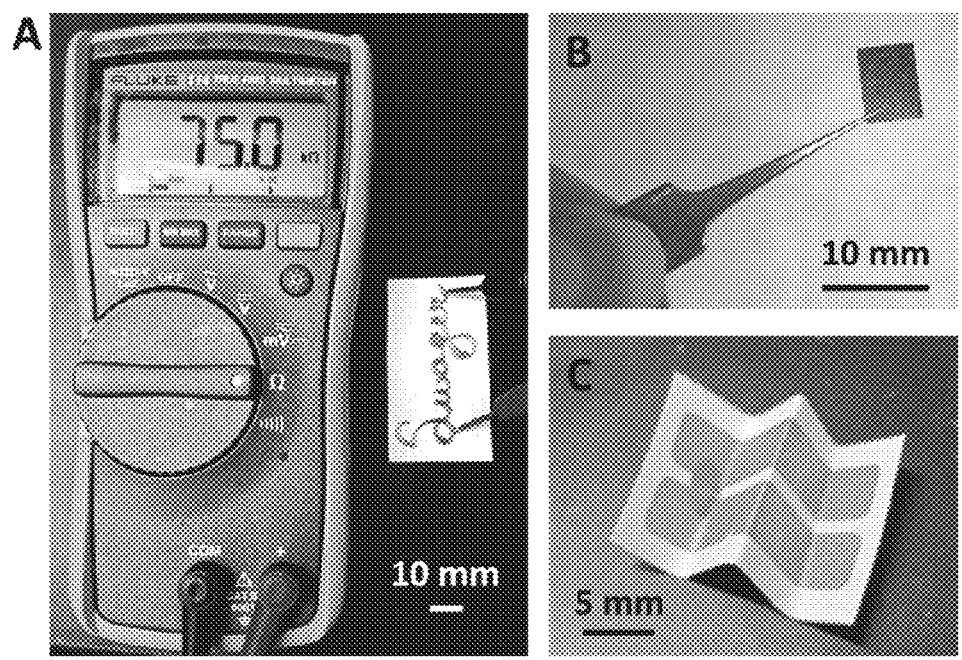
FIG. 1 shows photographs of sensors fabricated by mechanical abrasion of graphite-based pencil on copy paper.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein may be useful in the fabrication of devices (e.g., sensors, circuits, etc.) including conductive materials. In some cases, devices and methods for determining analytes are provided. Methods described herein may allow for rapid prototyping, fabrication, and screening of devices including various conductive materials, and may be useful in fabricating sensors, circuits, tags for remotely-monitored sensors or human/object labeling and tracking, among other devices. Furthermore, parallel fabrication of multiple devices can generate cross-reactive arrays capable of sensing and differentiating analytes at part-per-million and part-per-billion concentrations.

In some cases, methods described herein may provide the ability to produce a variety of devices unconstrained by the limits of previous methods. For example, a wide range of conductive patterns may be formed on a substrate without being limited by the capabilities of lithographic methods or ink jet printing. In some embodiments, the devices may be fabricated in the absence of solvents (e.g., toxic solvents, surfactants, and the like), eliminating the need for prolonged drying times and/or prolonged sonication times and/or unsafe exposure to toxic solvents that pose a risk to human health or the environment. The resulting devices may be flexible, bendable, and stackable, while maintaining various electrochemical properties (e.g., conductance) when the device is bent, creased, or otherwise physically distorted from its original shape. In some cases, the methods may allow for fabrication of devices having readily tunable electronic properties.

Another advantageous feature provided by methods described herein is the ability to readily incorporate (e.g., process) conductive materials such as carbon nanotubes, as well as other components, into devices. For example, a device may include materials (e.g., carbon nanotubes, graphene, nanostructured graphite, etc.) which might otherwise be difficult to process using previous methods, for example, due to insolubility of the materials and/or complex synthetic procedures needed to fabricate the materials. Some embodiments of the invention provide simplified fabrication methods for devices comprising materials such as carbon nanotubes.

Figure 9:
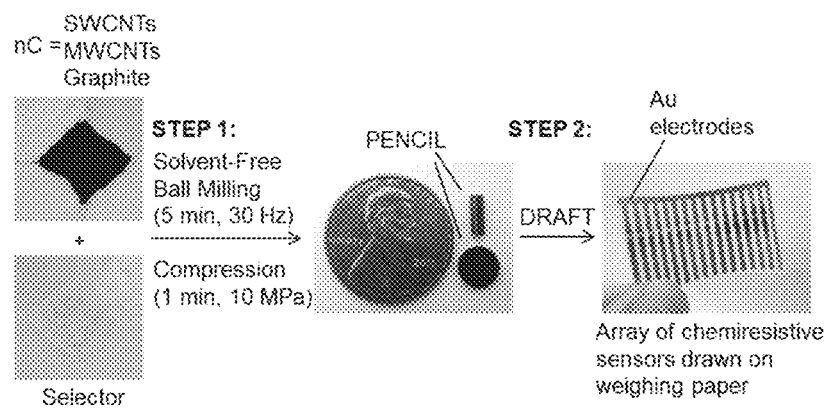
FIG. 9 shows a schematic outline of an exemplary process for rapid prototyping of selective carbon-based chemiresistors on the surface of paper.

Methods described herein may be useful in the rapid screening of materials suitable for use in various devices. For example, a plurality of devices, each containing a different material, or combination of materials, may be quickly and inexpensively fabricated in order to evaluate a wide range of materials suitable for use in a particular application. In some cases, a single device may be fabricated within about 60 minutes, about 45 minutes, about 30 minutes, about 15 minutes, within about 10 minutes, or within about 5 minutes. In some cases, a plurality of prototype sensor devices may be rapidly fabricated, each containing a different sensing material, and the sensing performance of each device may be evaluated upon exposure to a particular analyte in order to identify suitable sensing materials for a particular analyte. FIG. 9 shows an illustrative embodiment of such a screening process, involving generation of solid composites of a conductive material (e.g., nanotubes or graphite) and a species selected to interact with specific classes of analytes (e.g., vapor phase analytes) by solvent-free mechanical mixing (e.g., in a ball mill) and subsequent compression. The resulting solid composites may be used to form a sensor (e.g., a chemiresistive sensor) by mechanical abrasion of the solid composites onto the surface of paper, plastic, or other solid articles (substrates).

Various methods for fabrication of devices are provided. In some cases, the method involves contacting an article (e.g., a solid article) which includes a conductive material with a surface of a substrate, thereby forming the conductive material on the surface of the substrate. In some embodiments, the article is contacted with the substrate in the absence of a solvent. In some embodiments, the article is contacted with the substrate using mechanical abrasion (e.g., physical abrasion). For example, a surface of the article may be rubbed along the surface of the substrate to deposit the conductive material on the substrate. In some cases, the conductive material may be drawn on the surface of the substrate with the article, either manually or by an automated device.

The conductive material may be formed on at least one surface of the substrate. In some cases, the conductive material may be formed on one surface of the substrate. In some cases, the conductive material may be formed on two or more surfaces of the substrate. For example, the substrate may be paper, and the conductive material may be formed on opposing sides of the paper substrate.

The conductive material may be any material capable of conducting charge, including inorganic materials (e.g., metals, alloys, semiconductors), organic materials, organometallic materials, and/or combinations thereof. For example, the conductive material may include nanostructures (e.g., nanotubes, nanoparticles, graphene, etc.), polymers (e.g., conductive polymers), metal-containing species (e.g., metals, metal salts, etc.), biological species (e.g., proteins, DNA, RNA, etc.), and/or small molecules. In some cases, the conductive material comprises a carbon-based material. For example, the conductive material may include a nanostructured form of carbon, such as carbon nanotubes, graphite, or graphene. In some embodiments, the conductive material comprises carbon nanotubes, including single-walled carbon nanotubes and/or multi-walled carbon nanotubes. The carbon nanotubes may be provided as a solid, dispersion, suspension, an aligned array, or a randomly-oriented network, The method may further involve forming an electrical circuit that includes the conductive material. In some cases, an electrode material may be arranged to be in electrochemical communication with the conductive material, and a potential may then be applied to the electrode material. "Electrochemical communication," as used herein, refers to materials that are in sufficient communication with each other, such that the transfer of electrons, polarons, excitons, and/or protons can occur between the two materials. For example, the first and second electrodes may not physically contact one another but may be in electrochemical communication with one another via the conductive material, such that upon application of a voltage or potential, a current flows from the one electrode through the conductive material to the other electrode.

In some embodiments, the method may further involve arranging one or more species or "selectors" responsive to an analyte, or analytes, and/or to a change in a set of conditions in the surrounding environment, in electrochemical communication with the conductive material such that, in the presence of the analyte or upon occurrence of the change in the set of conditions, a determinable signal of the device is produced. The signal may, in some cases, provide information relating to the presence, identity, amount, and/or other characteristic of the one or more analytes. In some cases, the signal may indicate a change in the environment in which the device is placed. Signals produced by the device can be monitored and read by various methods, including optical methods, or electric or electrochemical methods using, for example, standard electronic characterization techniques or an RFID reader.

The species (e.g., "selector") may be any moiety that may interact with an analyte and/or that may be responsive to a change in a surrounding medium or environment, and may be incorporated within the device in various configurations. For example, the species may be a small molecule, a polymer, a biological species, or the like. In some embodiments, the species may comprise ionic species (e.g., a salt). In some embodiments, the species may comprise a neutral species. The species may be an organic, organometallic, or an inorganic species. In some cases, the species may be attached to the conductive material via a bond. In some cases, the species may be substantially contained within (e.g., dispersed within) the conductive material, and may not form a covalent bond to the conductive material. In some embodiments, an article containing both the conductive material and the species may be provided, such that contacting the article with the surface of a substrate via mechanical abrasion results in the formation of the conductive material and the species on the surface of the substrate.

In some cases, the mass ratio of the conductive material to the species (e.g., selector) is about 1:0, about 1:1, about 1:2, about 1:3, about 1:4, about 1:5, about 1:6, about 1:7, about 1:8, or, in some cases, about 1:9. In certain embodiments, it may be desirable to have a mass ratio of conductive material to species that is about 1:0, about 1:1, about 1:2, or about 1:5).

The interaction between the analyte and the species may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), and the like. The interaction may also comprise Van der Waals interactions. In one embodiment, the interaction comprises forming a covalent bond with an analyte. In some cases, the interaction between the device and the analyte may comprise a reaction, such as a charge transfer reaction. In other embodiments, the species and/or another device component may undergo a chemical or physical transformation upon a change in the surrounding environment (e.g., change in temperature) to produce a determinable signal from the device.

In some embodiments, the analyte may contact, or may be positioned in sufficient proximity to, the species, or may permeate an interior portion of the device. In some embodiments, a volumetric or dimensional change (e.g., increase, decrease) of the device may occur upon interaction with an analyte. For example, a component of the device may "swell" upon absorption of the analyte, wherein the change in volume may produce a change in a property of the device.

In some cases, the species may comprise a biological or a chemical group capable of binding another biological or chemical molecule in a medium (e.g., solution, vapor phase, solid phase). For example, the species may include a functional group, such as a thiol, aldehyde, ester, carboxylic acid, hydroxyl, and the like, wherein the functional group forms a bond with the analyte. In some cases, the species may be an electron-rich or electron-poor moiety wherein interaction between the analyte and the species comprises an electrostatic interaction. In some cases, the interaction between the analyte and the species includes binding to a metal or metal-containing moiety.

The species may also interact with an analyte via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of species include peptides, proteins, DNA, RNA, PNA.

In some embodiments, the species may be an aromatic species substituted with one or more halo-containing groups. In one set of embodiments, the species is a fluorine-containing aromatic species. For example, the species may be an aromatic species substituted with one or more fluoro groups, or an aromatic species substituted with a group comprising one or more fluoro groups. In some cases, the fluorine-containing aromatic species is an aromatic species substituted with one or more fluoro groups, fluoroalkyl groups, and/or fluorinated alcohol groups (e.g., hexafluoro-isopropanol). For example, the fluorine-containing aromatic species may be a fluoro-substituted naphthalene. In another example, the fluorine-containing aromatic species may be a naphthalene species substituted with a hydroxyl group and a fluorinated alcohol group. Illustrative embodiments of fluorine-containing aromatic species include

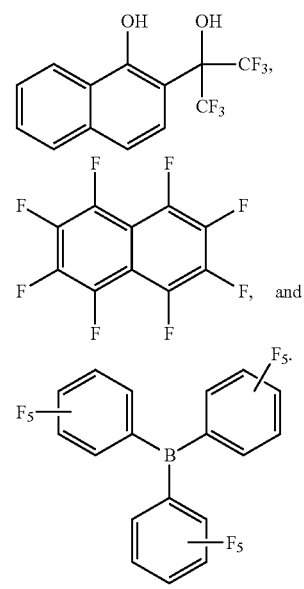

In some embodiments, the species may comprise a fluorinated alcohol group, such as a hexafluoroisopropanol group. In some cases, the species comprising the fluorinated alcohol group is

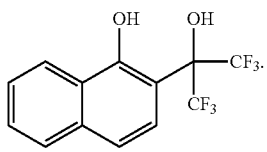 [SMILES: Oc1c(C(O)(C(F)(F)F)C(F)(F)F)ccc2ccccc12]

In some embodiments, the species may be a metal-containing species. For example, the species may be a metal-containing species, including metal salts. In some embodiments, the metal salt is a transition metal salt or complex. Some examples of metal salts include, but are not limited to, $TiO_2$, $TiCl4$, and other titanium salts, $AgCl$, $AgPF_6$, $Ag(OCOCF_3)$, $Ag(SO_3CF_3)$, and other silver salts, $PtCl_2$ and other platinum salts, $Au_2Cl_6$ and other gold salts, $Al(OEt)_3$ and other aluminum salts, $Ni(SO_3CF_3)_2$, $NiCl_2$, and other nickel salts, and $Cu(SO_3CF_3)$ and other copper salts, In some cases, the species may be a copper-containing species. In some cases, the copper-containing species is a salt, such as a Cu(II) salt. In some cases, the species may be a palladium-containing species. In some cases, the palladium-containing species is a salt, such as a Pd(II) salt. Some examples of specific metal containing species include, but are not limited to,

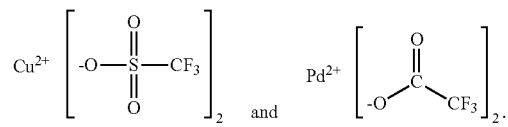

In some embodiments, the species may be a metal complex capable of interacting with ethylene. An example of such a metal complex is described in Esser et al., "Selective Detection of Ethylene Gas Using Carbon Nanotube-based Devices: Utility in Determination of Fruit Ripeness," Angew. Chem. Int. Ed. 2012, 51(23), 5752-5756, the contents of which are incorporated herein by reference in its entirety for all purposes.

In some embodiments, the species may be an optionally substituted polycyclic aromatic group, such naphthalene, phenanthrene, pyrene, anthracene, fluoranthene, perylene, benzopyrene, any of which is optionally substituted, and the like.

In some embodiments, the species may be a quinone-containing species or an oxidized derivative of an aromatic group, including polycyclic aromatic groups. Examples of such species include 1,4-benzoquinones or cyclohexadienediones, 1,2-benzoquinones (ortho-quinones), 1,4-naphthoquinones and 9,10-anthraquinones. And the like. In one embodiment, the species is 2,3-dichloro-5,6-dicyano-1,4-benzoquinone (DDQ).

Figure 10:
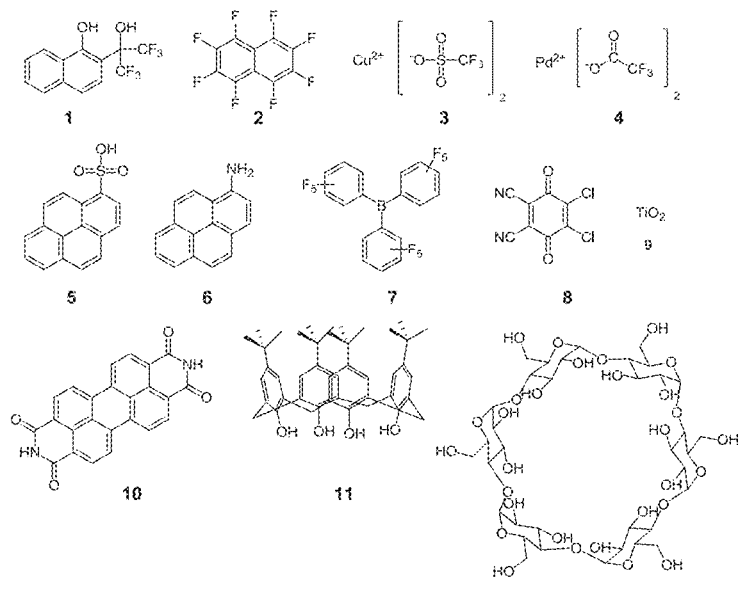
FIG. 10 shows examples of molecular "selectors" useful in certain embodiments described herein.

FIG. 10 shows examples of such species or selectors suitable for use in the context of the embodiments described herein.

In some cases, fabrication methods described herein may advantageously allow for rapid screening of a wide range of materials or combination of materials for use in a particular application and/or device. For example, rapid prototyping of a large number of chemiresistive gas and vapor sensors can be achieved. As shown in FIG. 9, physical or mechanical abrasion of an article containing a sensing material on the surface of a substrate may be rapidly performed to produce a prototype device. The prototype devices may each contain a different conductive material, a different selector or species, different mass ratios of conductive material to selector/species, and/or may differ in other device characteristics, such as film thickness, electrode materials, device configuration, and the like. Evaluation of the performance of each prototype device may be performed to identify the device appropriate for use in a particular application. Subsequent fabrication of larger devices, or larger numbers of devices, may optionally be performed using a similar fabrication method as described herein, and/or other methods, including chemical vapor depositions, drop-casting, spin-coating, spray-coating, inkjet printing, transfer printing, and the like.

In some cases, fabrication methods described herein may also allow for screening of a wide range of conditions (e.g., reaction time, temperature, analyte concentration, etc.) that may be suitable for a particular application. For example, in the case of sensors, a plurality of identical prototype devices may be fabricated using methods described herein, and each prototype device may be placed under a different set of conditions in order to optimize device performance. In some cases, the prototype devices may be placed under conditions which vary in temperature, pH, type of atmosphere (e.g., nitrogen, oxygen, etc.), potential, current, analyte, exposure time to analyte, concentration of analyte, and the like.

Devices for determining analytes are also provided. Typically, the device may include a first electrode, a second electrode, and a sensor material arranged in electrochemical communication with the first and the second electrodes. The sensor material may include a conductive material (e.g., a carbon-based nanostructure), such that resistance to current flow between the first and second electrode is affected by the sensor material. Upon exposure to an analyte, the analyte may interact with the sensor material to affect resistance to current flow between the first and second electrodes, thereby generating a signal in the device by which the analyte is determined. In some embodiments, the sensor material is in substantially solid form.

In some cases, the sensor material may include carbon-based nanostructures as the conductive material. For example, the conductive material may include nanotubes, nanoparticles, graphene, or graphite. In some embodiments, the conductive material includes nanotubes. In some embodiments, the conductive material includes single-wall carbon nanotubes. In some embodiments, the conductive material includes multi-wall carbon nanotubes. In some embodiments, the conductive material includes graphite. In some embodiments, the conductive material includes graphene. The sensor material may further include a species or "selector" as described herein. The species may be selected to be responsive to a particular analyte, set of analytes, and/or to a change in a set of conditions in the surrounding environment, and may be integrally connected to at least a portion of the conductive material such that, in the presence of the analyte or upon occurrence of the change in the set of conditions, a determinable signal of the device is produced.

As used herein, the term "integrally connected," when referring to two or more components, means components that do not become separated from each other during the course of normal use, e.g., separation requires at least the use of tools, or by breaking bonds, by dissolving, etc. In some embodiments, the conductive material and the species may be covalently attached to one another. In some embodiments, the conductive material and the species may be non-covalently associated with one another. For example, the species may be dispersed throughout a portion of the conductive material. Alternatively, the conductive material may be dispersed throughout a portion of the species. In some cases, the conductive material and the species may be combined together as a blend in solid form, e.g., as a blended power. In some cases, the conductive material and the species may be mechanically mixed (e.g., ball milled), and then formed into a solid upon application of pressure (e.g., via a hydraulic press).

In one set of embodiments, the sensor material comprises a conductive material and a fluorine-containing aromatic species integrally connected to at least a portion of the conductive material. In some embodiments, the sensor material comprises carbon-based nanostructures (e.g., single-walled carbon nanotubes) and a fluorine-containing aromatic species integrally connected to at least a portion of the conductive material. Devices including such sensor materials may be useful, for example, in the determination of aromatic species.

In another set of embodiments, the sensor material comprises a conductive material and a copper-containing species integrally connected to at least a portion of the conductive material. In some embodiments, the sensor material comprises carbon-based nanostructures (e.g., single-walled carbon nanotubes) and a copper-containing species integrally connected to at least a portion of the conductive material. Devices including such sensor materials may be useful, for example, in the determination of amine-containing species such as ammonia.

In another set of embodiments, the sensor material comprises a conductive material and a palladium-containing species integrally connected to at least a portion of the conductive material. In some embodiments, the sensor material comprises carbon-based nanostructures (e.g., single-walled carbon nanotubes) and a palladium-containing species integrally connected to at least a portion of the conductive material. Devices including such sensor materials may be useful, for example, in the determination of nitrile-containing species, such as acetonitrile.

In another set of embodiments, the sensor material comprises a conductive material and a species comprising a fluorinated alcohol group integrally connected to at least a portion of the conductive material. In some embodiments, the sensor material comprises carbon-based nanostructures (e.g., single-walled carbon nanotubes) and a species comprising a fluorinated alcohol group integrally connected to at least a portion of the conductive material. Devices including such sensor materials may be useful, for example, in the determination of analytes including oxygen-containing species, such as ketones, esters, ethers, and the like.

In some embodiments, the sensor material comprises a conductive material and a species integrally connected to at least a portion of the conductive material, wherein the species is

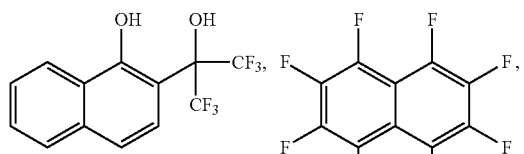

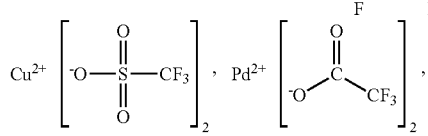

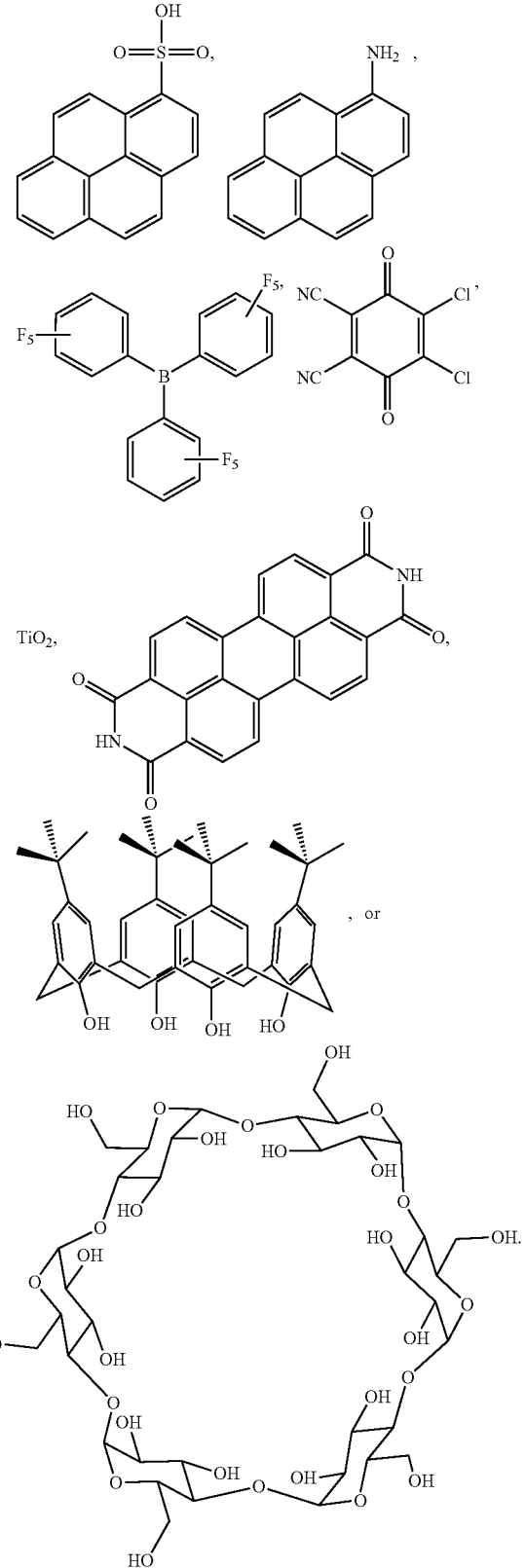

In some embodiments, the sensor material comprises carbon-based nanostructures (e.g., single-walled carbon nanotubes) and a metal complex (e.g., copper complex) integrally connected to at least a portion of the conductive material. Devices including such sensor materials may be useful, for example, in the determination of ethylene.

An analyte, or a change in the environment surrounding the device, may be determined by monitoring, for example, a change in a signal of a species or material present within the device. The change in signal may be associated with an interaction (e.g., covalent bonding, non-covalent bonding) between the device (e.g., species) and the analyte. The signal may comprise an electrical, optical, or other property of the device. For example, the device may have a resistance that is affected by the presence of an analyte. As used herein, the term "determining" generally refers to the analysis of a species or signal, for example, quantitatively or qualitatively (whether the analyte is present and/or in what amount or concentration), and/or the detection of the presence or absence of the species or signals. "Determining" may also refer to the analysis of an interaction between two or more species or signals, for example, quantitatively or qualitatively, and/or by detecting the presence or absence of the interaction. For example, the method may include the use of a device capable of producing a first, determinable signal (e.g., a reference signal), such as an electrical signal, an optical signal, or the like, in the absence of an analyte. The device may then be exposed to a sample suspected of containing an analyte, wherein the analyte, if present, may interact with one or more components of the device to cause a change in the signal produced by the device. Determination of the change in the signal may then determine the analyte. In some cases, devices described herein may be useful as sensors for analytes such as explosives, chemical warfare agents, and/or toxins.

In some cases, the analyte may be present in a part-per-million concentration. In some cases, the analyte may be present in a part-per-billion concentration.

In some embodiments, interaction between the device and an analyte produces a change in an electrical or electrochemical property of the device. For example, the conductive material (e.g., carbon nanotube) may be arranged in electrical communication with two electrodes and may have a particular current, voltage, conductivity, and/or resistance (e.g., signal). Upon interaction with an analyte, the current, voltage, conductivity, and/or resistance of the device may be affected (e.g., may increase or decrease) such that a change in signal is produced. In some cases, the change in signal may be associated with a charge transfer reaction and/or binding interaction between the conductive material and the analyte. In some cases, the change in the signal may be associated with a change in the orientation and/or arrangement of the conductive material. In some cases, the change in signal may, be attributed to a physical or chemical disruption in the conductive pathways between conductive species (e.g., carbon nanotubes) of the device.

In some cases, the device may comprise additional components or species that may facilitate interaction between the device and analyte, or otherwise enhance performance of the device. In some cases, the additional component may improve the ability of the device to produce a signal or to respond to an analyte. The additional component may associate with the device such that it enhances an electrical, optical, or other property of the device. In some cases, the additional component may act as a dopant for a conductive species (e.g., carbon nanotube) present within the device. For example, the device may comprise a species capable of associating with carbon nanotubes present within the device. In some embodiments, the device includes a species that may interact with the carbon nanotubes via pi-stacking interactions.

The device may comprise additional components, such as a detector component positioned to detect the signal. In one set of embodiments, the device may be a chemiresistor device, wherein the device exhibits changes in electrical resistance upon exposure to an analyte. Chemiresistors may be advantageous in that the resistance changes can be read-out by a simple, low power and low current circuit. In other embodiments, a device of the present invention may exhibit signals, or changes in signals, that may be determined using Raman spectroscopy, adsorption and/or emission photophysics, ellipsometry, atomic force microscopy, scanning electron microscopy, electrode passivation, and the like.

In some embodiments, simple screening tests may be conducted to select appropriate conductive materials (e.g., carbon nanotubes), species, device configuration, set of conditions, etc., to suit a particular application. In some cases, a material or device may be screened to determine the sensitivity and/or stability of the material or device. In some cases, a material (and/or device) may be selected based on an ability to detect one or more analytes. For example, the ability of a device to detect an analyte may be determined by comparing the signal (e.g., conductance) of the device prior to and following exposure to an analyte. In another example, a device may be exposed to varying concentrations of an analyte to determine the sensitivity of the device.

In some cases, the device may determine changes in a condition, or set of conditions, of a surrounding medium. As used herein, a change in a "condition" or "set of conditions" may comprise, for example, change to a particular temperature, pH, solvent, chemical reagent, type of atmosphere (e.g., nitrogen, argon, oxygen, etc.), electromagnetic radiation, or the like. In some cases, the set of conditions may include a change in the temperature of the environment in which the device is placed. For example, the device may include a component (e.g., species) that undergoes a chemical or physical change upon a change in temperature, producing a determinable signal from the device.

Articles suitable for use in methods described herein may be fabricated using various methods. Typically, the article comprising the conductive material is in solid form (e.g., a pellet, pencil, etc.), and may, in some cases, exhibit improved stability relative to solutions, suspensions, dispersions, slurries, etc., containing such conductive materials. The article may be referred to herein as a "Process Enhanced NanoCarbon for Integrated Logic" or "PENCIL." In some embodiments, the article is prepared by compression of a powder that includes the conductive material. In some embodiments, the article is prepared by mechanical mixing (e.g., ball milling) a powder that includes the conductive material, followed by compression of the powder to form the article. In some embodiments, the article is prepared from a solution including the conductive material. Such articles or "PENCILs" can be used repeatedly for the fabrication of multiple sensors, using methods described herein. In some cases, a functional device (e.g., sensor) may be fabricated using a relatively small amount of material, e.g., <5 μg.

In some cases, the article contains both the conductive material (e.g., a carbon-based nanostructure or nanostructured carbon) and the species responsive to an analyte or to a change in a surrounding medium or environment. For example, the article may be a solid composite of the conductive material and the species. In one set of embodiments, the conductive material may be mechanically mixed (e.g., ball milled) with a species or selector, forming a blended powder. In some cases, the mechanical mixing may involve ball milling, including liquid- or solvent-assisted ball milling as well as ball milling at different temperatures. In some embodiments, the method may involve ball milling a conductive material and species, if present, that have been cooled cryogenically prior to mixing, for example, to enhance inelastic collision efficiency. In some embodiments, the method may involve ball milling a conductive material and species, if present, that have been heated, for example, to add energy to the system and facilitate annealing.

The blended powder may then been compressed into an article (e.g., pellet, rod, or other shape) with a hydraulic press, and subsequently deposited onto a substrate by mechanical abrasion to produce a conductive layer of material selective for specific analytes or specific changes in a set of conditions. For example, carbon nanotubes may be ball-milled with various molecules designed for selective capture of vapors, and the resulting blended powder may be compressed into a pellet. Mechanical abrasion between the pellet and a substrate may be performed to form a conductive material responsive to an analyte or changes in a set of conditions.

In some embodiments, the conductive material, and optionally additional components, may be combined with a fluid carrier (e.g., solvent) and stirred, vortexed, sonicated, or the like. The resulting mixture may be subsequently dried into a solid form by evaporation, spray drying, heating, freeze-drying, compression, or other methods, to produce the article.

Devices as described herein may have various device configurations, and may be selected to suit a particular application. For example, the conductive material may be fabricated such that a first and the second electrode are in electrochemical communication with the conductive material. The device may be used as a sensor, circuit, a capacitor, a tag for remotely-monitored sensors, a label or tracker for a subject or object, a photovoltaic device, a resistor, a fuse, a transistor, an antenna, or in other applications. Those of ordinary skill in the art would be able to select suitable materials (e.g., conductive materials, species, substrates, electrode materials, etc.) for a particular application.

In some embodiments, a plurality of devices may be arranged to form an array of devices capable distinguishing, identifying, and quantifying a variety of different analytes simultaneously. For example, in an array of devices, each individual device can include a species responsive to an analyte. In some cases, a first device of the array may include a species responsive to a first analyte and a second device of the array may include a species responsive to a second analyte, wherein the first and second analytes are different.

As described herein, in some cases, a single device may be fabricated within about 60 minutes or less (e.g., within about 60 minutes, within about 45 minutes, within about 30 minutes, within about 15 minutes, within about 10 minutes, within about 5 minutes). In such cases, the act of fabricating the single device consists essentially of the acts of (1) forming the article comprising the conductive material and, optionally, the species responsive to an analyte and/or to a change in a set of conditions; (2) forming the conductive material and species, if present, on the surface of the substrate with the article (e.g., via physical abrasion); and (3) arranging an electrode material in electrochemical communication with the conductive material and species, if present. In one embodiment, the first step may be performed in about 5 minutes, while the second and third steps may be performed in about 5 minutes; that is, the fabrication of a single device may be performed in about 10 minutes.

In some cases, the method may involve fabricating a plurality of devices. For example, multiple devices can be fabricated, each device including a different sensor material, and the performance of each device may be evaluated in order to screen for which sensor material is suitable for a particular application. In some cases, multiple chemiresistor devices may be fabricated, each device including a different sensor material, and the change in resistance of each device upon exposure to an analyte, or to a change in environment, may be evaluated in order to screen for which sensor material is suitable for a particular application.

As used herein, the term "nanostructure" refers to any chemical structure having at least one dimension on the order of nanometers. In some cases, the nanostructure has an elongated chemical structure having a diameter on the order of nanometers and a length on the order of microns to millimeters, resulting in an aspect ratio greater than 10, 100, 1000, 10,000, or greater. In some cases, the nanostructure may have a diameter less than 1 µm, less than 100 nm, 50 nm, less than 25 nm, less than 10 nm, or, in some cases, less than 1 nm. The nanostructure may have a cylindrical or pseudo-cylindrical shape. In some cases, the nanostructure may be a nanotube, such as a carbon nanotube. In some cases, the nanostructure is a nanorod, nanowire, or nanoribbon. In some cases, the nanostructure is a nanoparticle.

As used herein, the term "carbon nanotube" is given its ordinary meaning in the art and refers to a substantially cylindrical molecule, in some cases, comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of millimeters, resulting in an aspect ratio greater than about 100, greater than about 1000, greater than about 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The carbon nanotubes may be functionalized or substituted with a wide range of functional groups. Examples of functional groups that carbon nanotubes may be substituted with include peptides, proteins, DNA, RNA, peptide nucleic acids (PNA), metal complexes, ligands for metals, ligands for proteins, antibodies, polarizable aromatics, crown ethers, hydroxylamines, polymers, initiators for polymerizations, liquid crystals, fluorocarbons, synthetic receptors, and the like. The properties of the nanotubes may also be tailored based on the substitution of the fused, aromatic network. Those skilled in the art would recognize what types of functional groups would afford a particular, desired property, such as increased solubility, or the ability to determine an analyte.

Substituted carbon nanotubes may be synthesized using various methods, including those described in Zhang et al., J. Am. Chem. Soc. 2007, 129(25), 7714; International Publication No. WO2008/133779, which are incorporated herein by reference in their entirety for all purposes.

In some cases, the conductive material may comprise nanoparticles. As used herein, the term "nanoparticle" generally refers to a particle having a maximum cross-sectional dimension of no more than 1 μm. Nanoparticles may comprise inorganic or organic, polymeric, ceramic, semiconductor, metallic, non-metallic, magnetic, crystalline (e.g., "nanocrystals"), or amorphous material, or a combination of two or more of these. The nanoparticles may be also selected to be positively or negatively charged. Typically, nanoparticles may have a particle size less than 250 nm in any dimension, less than 100 nm in any dimension, or less than 50 nm in any dimension. In some embodiments, the nanoparticles may have a diameter of about 2 to about 50 nm. In some embodiments, the nanoparticles may have a diameter of about 2 to about 20 nm. The particle size may be measured by methods known in the art, such as electron microscopy.

Polymers or polymer materials, as used herein, refer to extended molecular structures comprising a backbone (e.g., non-conjugated backbone, conjugated backbone) which optionally contain pendant side groups, where "backbone" refers to the longest continuous bond pathway of the polymer. In some embodiments, the polymer is substantially non-conjugated or has a non-conjugated backbone. In some embodiments, at least a portion of the polymer is conjugated, i.e. the polymer has at least one portion along which electron density or electronic charge can be conducted, where the electronic charge is referred to as being "delocalized." A polymer may be "pi-conjugated," where atoms of the backbone include p-orbitals participating in conjugation and have sufficient overlap with adjacent conjugated p-orbitals. It should be understood that other types of conjugated polymers may be used, such as sigma-conjugated polymers.

The polymer can be a homo-polymer or a co-polymer such as a random co-polymer or a block co-polymer. In one embodiment, the polymer is a block co-polymer. An advantageous feature of block co-polymers is that they may mimic a multi-layer structure, wherein each block may be designed to have different band gap components and, by nature of the chemical structure of a block co-polymer, each band gap component is segregated. The band gap and/or selectivity for particular analytes can be achieved by modification or incorporation of different polymer types, as would be understood by those of ordinary skill in the art. The polymer compositions can vary continuously to give a tapered block structure and the polymers can be synthesized by either step growth or chain growth methods.

The number average molecular weight of the polymer may be selected to suit a particular application. As used herein, the term "number average molecular weight (Mn)" is given its ordinary meaning in the art and refers to the total weight of the polymer molecules in a sample, divided by the total number of polymer molecules in a sample. Those of ordinary skill in the art will be able to select methods for determining the number average molecular weight of a polymer, for example, gel permeation chromatography (GPC). In some cases, the GPC may be calibrated vs. polystyrene standards. In some cases, the number average molecular weight of the polymer is at least about 10,000, at least about 20,000, at least about 25,000, at least about 35,000, at least about 50,000, at least about 70,000, at least about 75,000, at least about 100,000, at least about 110,000, at least about 125,000, or greater.

In some embodiments, various components of the device are formed on a substrate. The substrate can comprise a wide variety of materials, as will be appreciated by those in the art, including printed circuit board (PCB) materials. Suitable substrates include, but are not limited to, glass, fiberglass, Teflon, ceramics, metals, glass, silicon, mica, plastics and polymers of any kind (including acrylics, polystyrene and copolymers of styrene and other materials, polypropylene, polyethylene, polybutylene, polycarbonate, polyurethanes, cellulose acetate, polyethylene terephthalate, and derivatives thereof, etc.), GETEK (a blend of polypropylene oxide and fiberglass), paper (e.g., weighing paper, or other cellulose-based papers), fabric, skin, among others. In one set of embodiments, the substrate is paper. In some embodiments, the substrate may include a semiconductor material.

The device may also comprise an insulating material. The insulating material may be arranged between the conductive material and one or more electrodes and/or the substrate. Examples of suitable insulating materials include, but are not limited to, polysilicate glass, silicon dioxide, silicon nitride, and the like.

As used herein, the term "electrode" or "electrode material" refers to a composition, which, when connected to an electronic device, is able to sense a current or charge and convert it to a signal. An electrode may be comprised of a conductive material or combination of materials such as, for example, metals. Non-limiting examples of suitable metals include gold, copper, silver, platinum, nickel, cadmium, tin, and the like. The electrodes may also be any other metals and/or non-metals known to those of ordinary skill in the art as conductive (e.g. ceramics). The electrodes may be deposited on a surface via vacuum deposition processes (e.g., sputtering and evaporation), solution deposition (e.g., electroplating or electroless processes), or screen printing. In a specific example, gold electrodes are deposited by thermal evaporation.

In some embodiments, the conductive material may comprise a conductive, semiconductive, semimetallic species, or other species capable of transporting charge to create a conductive pathway. The conductive, semiconductive, or semimetallic species may include inorganic materials (e.g., metals, alloys, semiconductors), organic materials (e.g., polymer materials), organometallic materials, and/or combinations thereof. In some cases, the conductive material may include a plurality of nanostructures (e.g., nanotubes, nanowires, nanoribbons, nanoparticles, etc.). The nanostructures may be selected to exhibit, for example, high charge mobilities and/or resistance to damage from ionizing radiation. In some cases, mixtures or assemblies of nanostructures may be utilized. Some embodiments may involve the use of carbon nanotubes, such as single-walled carbon nanotubes (SWCNTs) and/or multi-walled carbon nanotubes (MWCNTs), which can display relatively high charge mobilities (e.g., 100,000 $cm^2/Vs$ for SWCNTs). In some cases, nanowires, such as gold, silver, copper, bismuth, gadolinium nanowires, may be used as the conductive species. In some cases, the conductive, semiconductive, or semimetallic species may comprise nanoparticles (e.g., gold nanoparticles).

As used herein, an "analyte" can be any chemical, biochemical, or biological entity (e.g. a molecule) to be analyzed. The analyte may be in vapor phase, liquid phase, or solid phase. In some embodiments, the analyte is a vapor phase analyte. In some cases, the analyte may be a form of electromagnetic radiation. In some cases, the device may be selected to have high specificity for the analyte, and may be a chemical, biological, or explosives sensor, for example. In some embodiments, the analyte comprises a functional group that is capable of interacting with at least a portion of the device (e.g., a species). In some cases, the device may determine changes in pH, moisture, temperature, and the like, of a surrounding medium. The analyte may be a chemical species, such as an explosive (e.g., TNT), toxin, or chemical warfare agent. In a specific example, the analytes are chemical warfare agents (e.g., sarin gas) or analogs of chemical warfare agents (e.g., dimethyl methylphosphonate, DMMP).

In some embodiments, the analyte may be an aromatic species, including optionally substituted aryl species and/or optionally substituted heteroaryl species, such as benzene or toluene. In some embodiments, the analyte may be an amine-containing species such as ammonia. In some embodiments, the analyte may be a nitrile-containing species such as acetonitrile. In some embodiments, the analyte may be an oxygen-containing species, such as a species comprising an alcohol, a ketone, an ester, a carboxylate, an aldehyde, other carbonyl groups, an ether, or the like. In some embodiments, the analyte may be a species comprising a ketone, an ester, an ether, or an aldehyde, such as cyclohexanone, ethyl acetate, THF, or hexanal. In some embodiments, the analyte is a phosphorus-containing analyte such as DMMP. In some embodiments, the analyte may be a nitro-containing species such as nitromethane or TNT. Other examples of analytes include alcohols, olefins, nitric oxide, thiols, thioesters, and the like.

Specific examples of analytes include nitromethane, benzene, toluene, o-xylene, m-xylene, p-xylene, mesitylene, nitrobenzene, cyano-benzene, hexane, hexene, hexenal, ethylene, 1-methylcyclopropene, propene, butenes, isoprene, cyclohexanone, acetone, tetrahydrofuran (THF), methanol, ethanol, isopropanol, hexanal, DMMP, acetonitrile, nitromethane, ethyl acetate, methyl acetate, water, dimethylformamide (DMF), formaldehyde, dimethylsulfide, ethylene, or ammonia.

As used herein, an "aromatic species" includes unsubstituted or substituted, monocyclic or polycyclic aromatic ring or ring radical, including unsubstituted or substituted monocyclic or polycyclic heteroaromatic rings or ring radicals (e.g., aromatic species including one or more heteroatom ring atoms). Examples of aromatic species include phenyl, naphthyl, anthracenyl, chrysenyl, fluoranthenyl, fluorenyl, phenanthrenyl, pyrenyl, perylenyl, and the like.

As used herein, "aryl" means a monocyclic or polycyclic-aromatic ring or ring radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylthio, cyano, halo, amino, and nitro.

As used herein, "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like. Other embodiments suitable for use in the context of the embodiments described herein are described in International Pat. Apl. Serial No.: PCT/US2009/001396, filed Mar. 4, 2009, entitled, "Devices and Methods for Determination of Species Including Chemical Warfare Agents"; International Pat. Apl. Serial No.: PCT/US2009/006512, filed Dec. 11, 2009, entitled, "High Charge Density Structures, Including Carbon-Based Nanostructures and Applications Thereof"; U.S. patent application Ser. No. 12/474,415, filed May 29, 2009, entitled, "Field Emission Devices Including Nanotubes or Other Nanoscale Articles"; International Pat. Apl. Serial No.: PCT/US2011/051610, filed Oct. 6, 2010, entitled, "Method and Apparatus for Determining Radiation"; International Pat. Apl. Serial No.: PCT/US2010/055395, filed Nov. 4, 2010, entitled, "Nanostructured Devices including Analyte Detectors, and Related Methods"; International Pat. Apl. Serial No.: PCT/US2011/053899, filed Sep. 29, 2011, entitled, "COMPOSITIONS, METHODS, AND SYSTEMS COMPRISING POLY (THIOPHENES); and International Pat. Apl. Serial No.: PCT/US2011/025863, filed Feb. 23, 2011, entitled, "Charged Polymers and Their Uses in Electronic Devices", which applications are incorporated herein in their entireties for all purposes.

EXAMPLES AND EMBODIMENTS

Example 1

Various devices were fabricated using the methods described herein. FIG. 1 shows photographs of a range of different devices fabricated by mechanical abrasion of a graphite-based pencil on copy paper. FIG. 1A shows a conductive pattern generated by drawing with the graphite-based pencil on paper. FIG. 1B shows a device fabricated by depositing graphite on paper by abrasion with graphite-based pencil. FIG. 1C shows a conductive layer of graphite deposited by abrasion between and on top of two gold electrodes (electrodes fabricated by thermal evaporation), where the device remained conductive even when creased and folded.

Example 2

Figure 2:
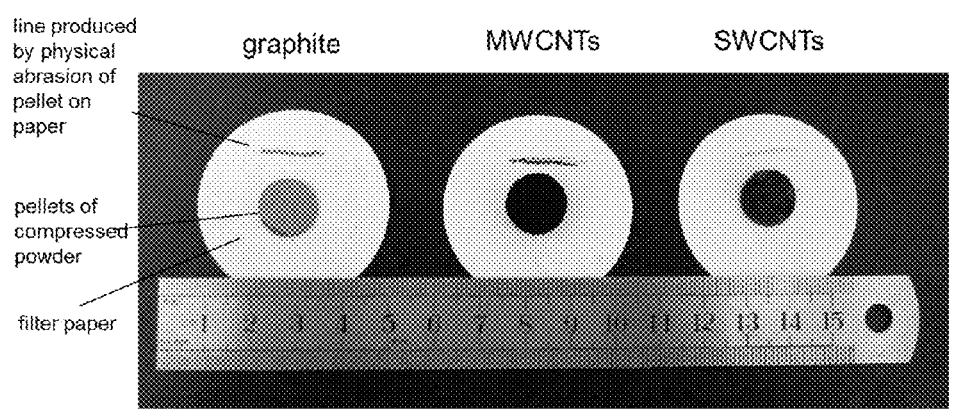
FIG. 2 shows a photograph of pellets of graphite, multi-walled carbon nanotubes (MWCNTs), and single-walled carbon nanotubes (SWCNTs) fabricated by compression of loose powders of these materials using a hydraulic press.

Articles including conductive materials for use in methods described herein were fabricated by compression of loose powders into pellets. FIG. 2 shows a photograph of pellets of graphite, multi-walled carbon nanotubes (MW-CNTs), and single-walled carbon nanotubes (SWCNTs) fabricated by compression of loose powders of these materials using a hydraulic press (compression for 1 minute at 6 metric tons). Such pellets may be used to deposit the carbon-based materials onto a substrate via mechanical abrasion.

Example 3

Figure 3:
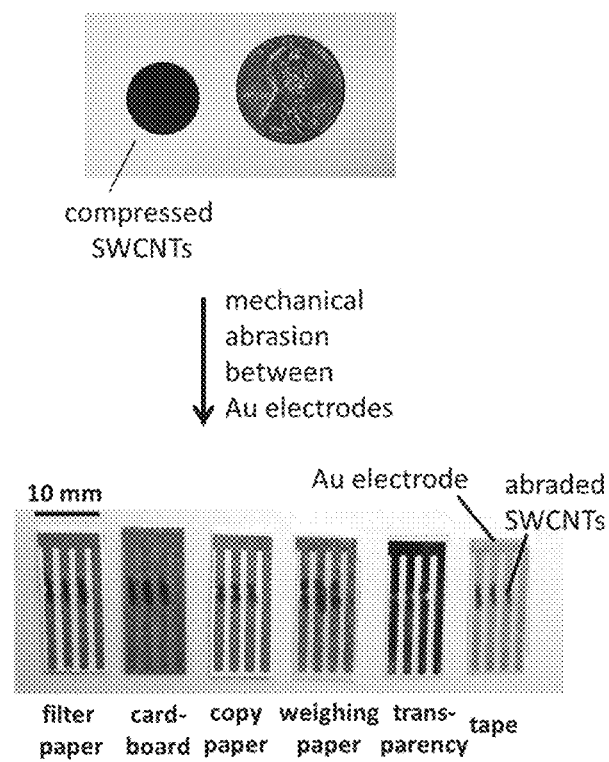
FIG. 3 shows photographs of devices formed by mechanical abrasion of a SWCNT-containing pellet onto various substrates.

FIG. 3 shows an overview of a process for fabricating sensors by mechanical abrasion of compressed SWCNTs on various paper and plastic substrates. The photographs illustrate the ability to fabricate sensors from SWCNTs on filter paper, cardboard, copy paper, weighing paper, transparency film, and mylar tape with adhesive backing.

Example 4

Figure 4:
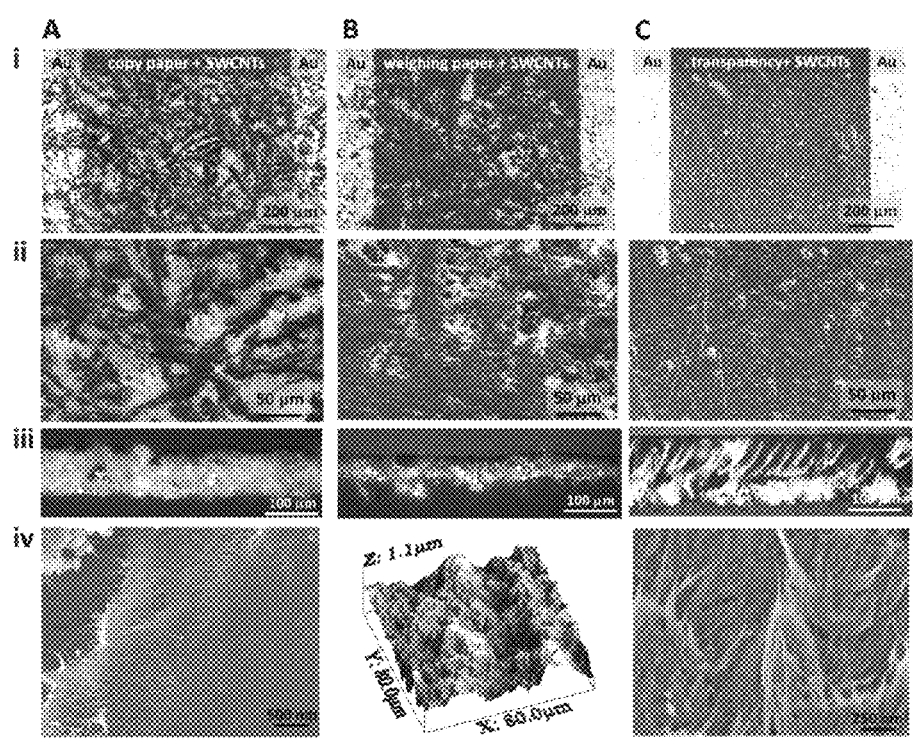
FIG. 4 shows various images of sensors fabricated by mechanical abrasion, including (a)(i) low-resolution SEM image of SWCNTs deposited on copy paper with 200 micron scale bar, (a)(ii) low-resolution SEM images of SWCNT deposited on copy paper with 50 micron scale bar, (a)(iii) an optical micrograph of the cross sectional view of SWCNTs deposited on copy paper, (a)(iv) high-resolution SEM image of SWCNTs deposited on copy paper; (b)(i) low-resolution SEM image of SWCNTs deposited on weighing paper with 200 micron scale bar, (b)(ii) low-resolution SEM image of SWCNTs deposited on weighing paper with 50 micron scale bar, (b)(iii) an optical micrograph of the cross sectional view of SWCNTs deposited on weighing paper, (b)(iv) an atomic force microscopy (AFM) image of the abrasion layer of SWCNTs on top of wax paper, illustrating sub-micron variations in surface roughness, (c)(i) low-resolution SEM image of SWCNTs deposited on plastic with 200 micron scale bar, (c)(ii) low-resolution SEM image of SWCNTs deposited on plastic with 50 micron scale bar, (c)(iii) an optical micrograph of the cross sectional view of SWCNTs deposited on plastic, (c)(iv) high-resolution SEM image of SWCNTs deposited on plastic.

This example describes the imaging and characterization of sensors fabricated by mechanical abrasion. FIG. 4 shows SEM imaging and characterization of sensors fabricated by mechanical abrasion of pristine SWCNTs on paper (FIG. 4A and FIG. 4B) and plastic (FIG. 4C). FIGS. 4Ai-4Ci and FIGS. 4Aii-4C show low-resolution SEM images of SWCNTs deposited on paper and plastic. FIGS. 4Aiii-Ciii show optical micrographs of the cross sectional view of SWCNTs deposited on paper and plastic. The thickness of the abrasion layer on paper was 1-10 µm, and >1 µm on transparency. FIG. 4A iv and FIG. 4C iv show high-resolution SEM images of SWCNTs deposited on copy paper and transparency showing bundles of individual SWCNTs. FIG. 4B iv shows an atomic force microscopy (AFM) image of the abrasion layer of SWCNTs on top of wax paper, illustrating sub-micron variations in surface roughness.

Example 5

Figure 5:
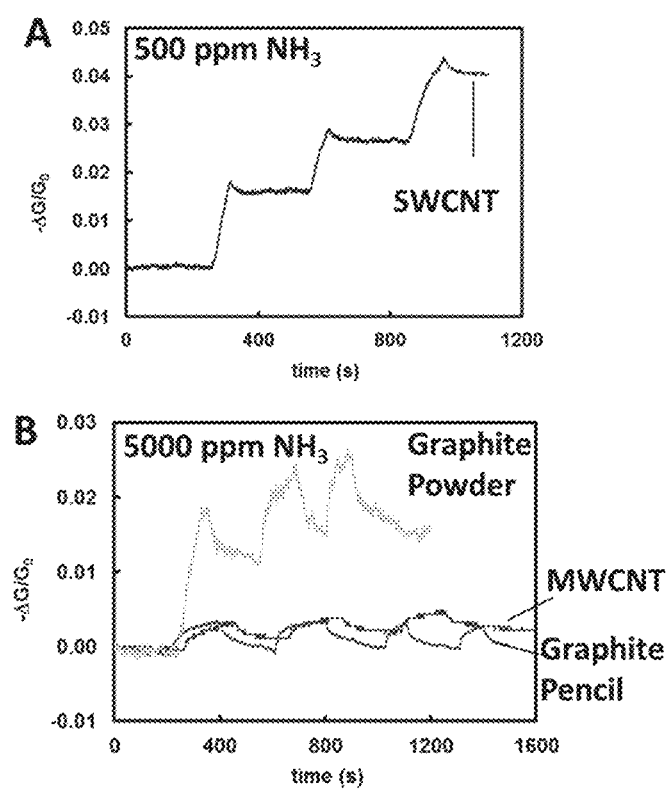
FIG. 5 shows the response of devices fabricated using methods described herein upon exposure to $NH_3$ vapor, including (a) data for the sensing of $NH_3$ using SWCNT after three exposures to 500 ppm of $NH_3$ gas lasting 100 s each, and (b) the response of MWCNTs, graphite, and compressed graphite powder after three exposures to 5000 ppm $NH_3$.

The following example describes the use of sensors fabricated using methods described herein. A conductive layer of either SWCNTs, MWCNTs, graphite (from a commercial graphite pencil), or compressed graphite powder was deposited on copy paper using mechanical abrasion. The conductive layers were then separately exposed to 500 ppm $NH_3$ (for SWCNTs) or 5000 ppm $NH_3$ vapor (for MWCNTs, graphite, and the compressed graphite powder) and the response of the device was recorded. FIG. 5A shows data for the sensing of $NH_3$ using SWCNT after three exposures to 500 ppm of $NH_3$ gas lasting 100 s each. FIG. 5B shows the response of MWCNTs, graphite, and compressed graphite powder after three exposures to 5000 ppm $NH_3$. Each of the devices displayed a detectable increase in conductivity upon exposure to $NH_3$, with the device containing SWCNTs showing the greatest increase in conductivity upon each exposure.

Example 6

Figure 6:
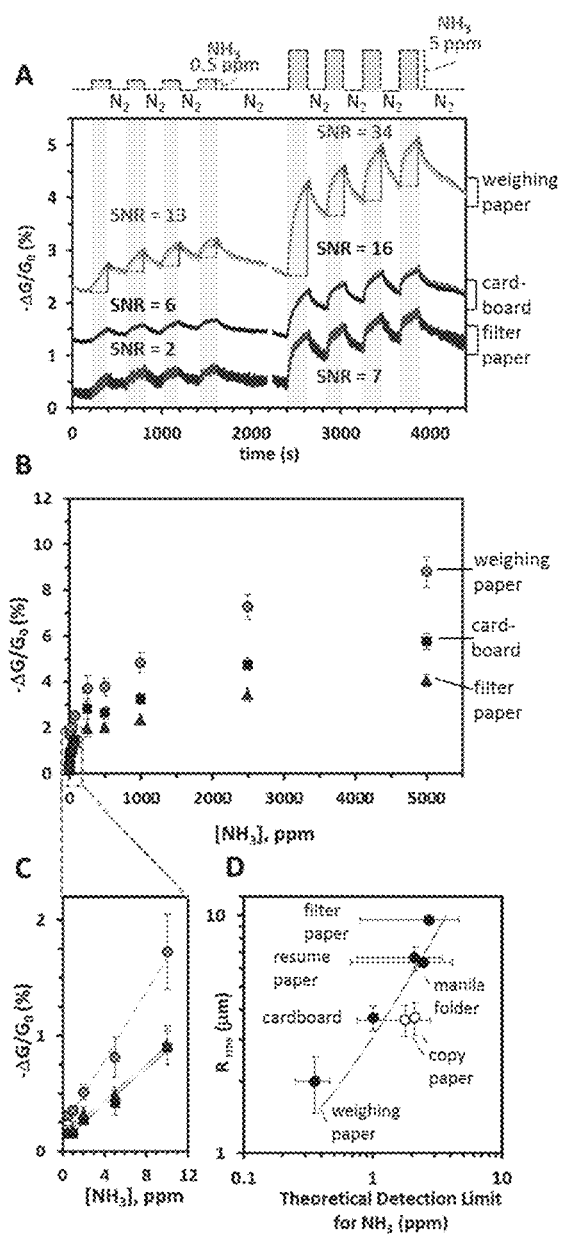
FIG. 6 shows the response of various devices towards ammonia, including (a) the normalized change in conductance with respect to time of devices exposed to 0.5 and 5 ppm $NH_3$ (4×200 s each); (b) the correlation of sensor response with [$NH_3$] (exposed for 200 s) for devices fabricated on three different types of paper; (c) the linear range of response of sensors drawn on weighing paper, filter paper, and cardboard; (d) a plot correlating the surface roughness of the paper substrates, on which the sensors were fabricated, with the theoretical detection limit of these sensors for $NH_3$ (o=fluorescent under UV light; ●=non-fluorescent).

The following example describes the use of devices fabricated using methods described herein in sensing ammonia. Four separate devices were fabricated by mechanical abrasion of compressed pristine SWCNTs on weighing paper, cardboard, copy paper, and filter paper, and the devices were exposed to various concentrations of ammonia. FIG. 6 shows the response of the devices towards $NH_3$ gas (diluted with $N_2$) FIG. 6A shows the normalized change in conductance (represented as $-\Delta G/G_0$, %) with respect to time of devices exposed to 0.5 and 5 ppm $NH_3$ (4×200 s each). The plot shows overlays of the responses of two separate devices for each type of paper. FIG. 6B shows the correlation of sensor response ($-\Delta G/G_0$, %) with [$NH_3$] (exposed for 200 s) for devices fabricated on three different types of paper. Vertical error bars represent standard deviations from the mean based on three exposures to $NH_3$ of three devices on each type of paper. The contribution of the signal from the first exposure to $NH_3$ at each concentration is excluded from the calculations of the mean signal and the standard deviation. FIG. 6C shows the linear range of response of sensors drawn on weighing paper, filter paper, and cardboard. $R^2=0.99$ for all three types of paper shown. FIG. 6D shows a plot correlating the surface roughness of the paper substrates, on which the sensors were fabricated, with the theoretical detection limit of these sensors for $NH_3$ (○=fluorescent under UV light; ●=non-fluorescent).

Example 7

Figure 7:
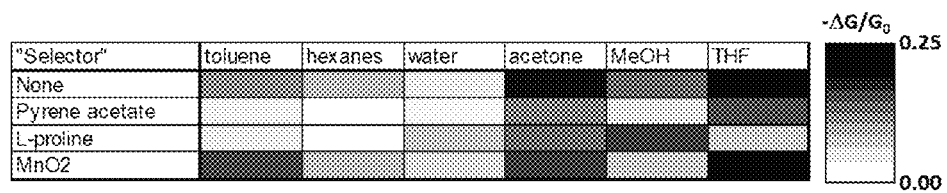
FIG. 7 shows the effect of ball-milling SWCNTs with "molecular selectors" on the selectivity and sensitivity of devices towards equilibrium vapors of various solvents.

In the following example, SWCNTs were ball milled with various analyte-responsive species or "molecular selectors" and the resulting mixture was compressed into a pellet. The SWCNT/molecular selector material was then deposited onto copy paper using mechanical abrasion. FIG. 7 shows the effect of ball-milling SWCNTs with various analyte-responsive species (or "molecular selectors") on the selectivity and sensitivity of these composite materials towards equilibrium vapors of various solvents. L-Proline was shown to enhance sensitivity of the device towards methanol, while suppressing sensitivity towards toluene. $MnO_2$ enhances sensitivity towards toluene, while suppresses sensitivity towards methanol.

Example 8

Figure 8:
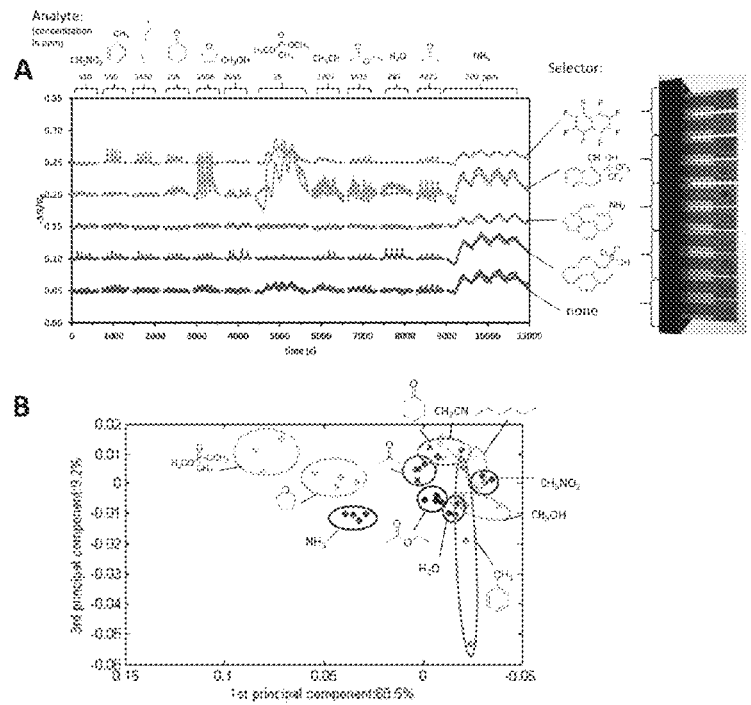
FIG. 8 shows (a) the change in conductance for various devices upon exposure to a particular analyte, and (b) the principal component analysis (PCA) for the devices.

The following example describes the fabrication of selective gas sensors by mechanical abrasion on ceramic substrates. Four sensing materials were used, each being a mixture of SWCNTs and an analyte-responsive small molecule ("molecular selector"). The analyte-responsive small molecules included a fluorinated naphthalene, a naphthalene substituted with a hydroxyl group and a fluorinated alcohol group, an amine-substituted pyrene, and an $SO_3H$-substituted pyrene. (FIG. 8A) Each sensing material was fabricated by solvent-free ball milling of pristine SWCNTs and one of the analyte-responsive small molecules for 5 min at 30 Hz at a 1:12 molar ratio of analyte-responsive small molecule:C of SWCNTs and subsequent compression of the blend into a pellet at 5 metric tons. The pellet then was abraded on top of a commercially available substrate comprising a set of interdigitated electrodes on a ceramic base (purchased from www.bvt.cz). The resulting devices were electrically connected to a potentiostat and the change in conductance ($-\Delta G/G_o$) towards various vapors (1-5% of equilibrium vapor pressure) was monitored for 10 devices simultaneously (5 sensing materials in duplicate). FIG. 8A shows the change in conductance for each device upon exposure to a particular analyte. FIG. 8B shows the principal component analysis (PCA) of the array of sensors.

Example 9

In this Example, the design, fabrication, and characterization of a chemiresistor device including a nC:selector composite as sensor material is described. Three different forms of nC were employed: single-walled carbon nanotubes (SWCNTs), multi-walled carbon nanotubes (MWCNTs), and graphite. Sensing materials are formed on the surface of paper using Deposition of Resistors with Abrasion Fabrication Technique (DRAFT), and can be performed in less than 5 minutes. This method is analogous to drawing with pencil on paper, and provides a convenient, reliable, and solvent-free method for fabricating devices described herein.

All chemicals and reagents were purchased from Sigma-Aldrich (Atlanta, Ga.) and used without further purification, unless noted otherwise. SWCNTs (purified ≥95% as SWCNT) were provided by Nano-C, Inc. (Westwood, Mass.). MWCNTs (>95% carbon, outer diameter=6-9 nm, average length=5 µm, number of walls=3-6) were purchased from Sigma-Aldrich (Atlanta, Ga.). Graphite Powder (natural, microcrystal grade, average particle size of 2-15 microns, 99.9995% [metal basis]) and Octafluoronaphthalene (CAS 313-72-4), 97% were purchased from Alfa Aesar (Ward Hill, Mass.). 2-(2-Hydroxy-1,1,1,3,3,3-hexafluoropropyl)-1-naphthol (CAS 2092-87-7), 97% was purchased from either SynQuest (Alachua, Fla.) or Santa Cruz Biotechnology (Santa Cruz, Calif.). Weighing Paper (Cat. No. 12578-165)—the substrate for the fabrication of sensors by mechanical abrasion—was purchased from VWR International (West Chester, Pa.). $NH_3$ (1% in $N_2$) and $NO_2$ (1% in air) were custom-ordered from Airgas.

Evaporation of Gold on Paper: Au electrodes (120 nm thickness) were deposited on the surface of paper through a stainless steel shadow mask (purchased from Stencils Unlimited, Lake Oswego, Oreg., http://www.stencilsunlimited.com/) using Thermal Evaporator (Angstrom Engineering, Kitchener, Ontario, Canada) under pressure of $1-4\times10^{-5}$ Torr and a rate of evaporation of 1-2 Å/s.

Ball Milling Selective sensing materials were generated by solvent-free ball milling of carbon (e.g., SWCNTs) with commercial small molecule "selectors" using an oscillating mixer mill (MM400, Retsch GmbH, Haan, Germany) within a stainless steel milling vial (5 mL) equipped with a single stainless steel ball (7 mm diameter). Unless otherwise indicated, a typical experiment involved filling the milling vial with carbon powder (e.g., SWCNTs) and selector (total mass of powder=150 mg) and ball milling the mixture for 5 min at 30 Hz.

Fabrication of Process Enhanced NanoCarbon for Integrated Logic (PENCILs): PENCILs were fabricated by loading powdered material into a mold, such as a pressing die set with 6-mm internal diameter (Across International, acrossinternational.com, Item #SDS6), or a pressing die set with 13-mm internal diameter, or a custom-build die set with 2-mm internal diameter, and compressing the powder by applying a constant pressure of 10 MPa for 1 min using a Hydraulic Press (Carver, Model #3912 or Across International Item #MP24A).

Microscopy: Scanning electron microscopy (SEM) was carried out using a JEOL JSM-6060 or JEOL JSM-6700F field emission SEM (FESEM) with energy-dispersive X-ray spectroscopy (EDX). Typical accelerating voltages were 1.5-5.0 kV.

Raman Spectroscopy: Raman spectra of solid composites were measured on a Horiba LabRAM HR Raman Spectrometer using excitation wavelength of 632.7 nm. The spectra were collected with the following parameters in place: filter=none; hole=1000 µm; slit=100 µm; grating=600; objective=10×. In real-time-display mode, the spectral signal at 0 $cm^{-1}$ was zeroed prior to acquisition. The spectrum was collected from 200 $cm^{-1}$ to 3000 $cm^{-1}$ with an integration time of 5 s averaged 100 times.

Measurements of Hardness of PENCILs: Ball-milled blends were compressed into pellets with thickness of ~1 mm using a hydraulic press. Measurements of mechanical hardness were carried out using Hysitron TriboIndenter equipped with a Berkovitch tip using quasi-static indentation with typical applied loads ranging between 2-10 mN and depth of indentation ranging between 0.5 and 5 µm.

Measurements of Resistivity: Measurements of bulk conductance of compressed blends were carried out using an osmium four-point probe (Signatone, Part number: SP4-50-045-OFS) with a tip radius of 0.127 mm, space between tips of 1.27 mm, and spring pressure of 45 grams. Bulk conductance σ (S/cm) of samples was calculated using Eq. 1 shown below. In this equation, V (V) is the voltage, I (A) is the current, w (cm) is the thickness of a circular sample composite, C (unitless) is the geometry correction factor that accounts for a finite diameter of a circular sample composite, and F (unitless) is the thickness correction factor that accounts for a finite thickness of a circular sample composite.

$$\sigma = I/(V \times w \times C \times F) \quad (1)$$

Design of Devices: The sensors in this example comprise conductive networks of carbon-based sensing materials deposited on the surface of paper-based chips equipped with gold electrodes. The sensors were configured as chemiresistors, which are a variable resistors that change their electrical resistance in the presence of chemical analytes, have minimal power requirements, and can be readily incorporated into miniaturized multiplexed arrays. Cellulose-based paper, which is commercially available and relatively inexpensive, was selected as the substrate for the fabrication of chemiresistive sensors in this example. The compatibility of paper with several well-established surface-processing technologies (e.g., drawing, printing, metal evaporation, chemical vapor deposition) facilitates rapid and straightforward introduction of diverse electronic features onto the surface of paper, and integration into chemiresistive sensing devices.

Although the use of electrodes is not required for the fabrication of functional chemiresistive sensors from graphitic materials on the surface of paper, it can be beneficial for several reasons, such as i) the minimization of the amount of sensing material required to produce a functional chemiresistor; ii) straightforward and rapid integration of devices into arrays; iii) low contact resistance at electrical connections. In this example, gold was selected as the material for the fabrication of electrodes on the surface of paper because it is chemically inert, has low contact resistance, and is easily deposited on the surface of paper by thermal evaporation. To create devices, paper-based chips were fabricated by depositing electrodes (with thickness of 120 nm, and a gap of 1 mm between electrodes) via thermal evaporation of gold through a shadow mask. Chemiresistors were then incorporated onto the surface of the paper-based chip by DRAFT between the gold electrodes.

FIG. 9 shows a schematic outline of the process for rapid prototyping of selective carbon-based chemiresistors on the surface of paper. The process involves two steps: (1) generating PENCILs by mechanical ball milling and subsequent compression of nanostructured carbon (nC) with small molecule selectors specifically chosen to interact with target analytes; and (2) using DRAFT (Deposition of Resistors by Abrasion Fabrication Technique) to produce an array of chemiresistors on the surface of weighing paper. The specific layout of the gold electrodes on paper was chosen to facilitate parallel integration of multiple chemiresistors onto a single chip. (FIG. 9) When connected to a potentiostat equipped with a multiplexer, this layout permitted evaluation of sensing performance of multiple chemiresistors simultaneously, and, thus, streamlined the characterization of device-to-device reproducibility and of the cumulative response from cross-reactive arrays.

Fabrication and Characterization of PENCILs: To define optimal characteristics of PENCILs for targeting specific analytes, the effect of the type of nC (e.g., graphite, SWCNTs, and MWCNTs) and the concentration of S (i.e., nC/S ratio) on materials properties and sensing response of the resulting composites was evaluated. The study was focused on nC/S composites generated by ball-milling selector 1 ($S^1$) as shown in FIG. 10 with graphite, SWCNTs, and MWCNTs at four different mass ratios (1:0, 1:1, 1:2, and 1:5) for 5 minutes at 30 Hz. Selector 1 was selected for this study as incorporation of a hexafluoroisopropyl moiety onto the surface of carbon nanotubes (e.g., covalently or non-covalently) can enhance the response of these materials toward O-containing H-bond acceptors, such as dimethyl methylphosphonate (DMMP), tetrahydrofuran (THF), and ketones. Without wishing to be bound by theory, the naphthyl moiety within selector 1 is capable of enabling favorable dispersive interactions with the conjugated $sp^2$ framework of nC, while the hexafluoroisopropyl moiety is capable of facilitating favorable H-bonding interactions with target analytes (e.g., acetone, THF, DMMP).

PENCILs were generated from nC/S blends by compression into the shape of a pellet within a stainless steel die for 1 min at 10 MPa. Although fabrication of PENCILs in the shape of a conventional cylindrical pencil lead compatible with commercial mechanical pencil holders is also possible (FIG. 9), molding composites into the shape of a pellet yielded a flat surface amenable to various methods of characterization. The materials properties of the resulting PENCILs were characterized using Raman spectroscopy, energy-dispersive X-ray (EDX) spectroscopy, scanning electron microscopy (SEM), conductivity measurements, and mechanical analysis (FIGS. 11-15).

Figure 11A:
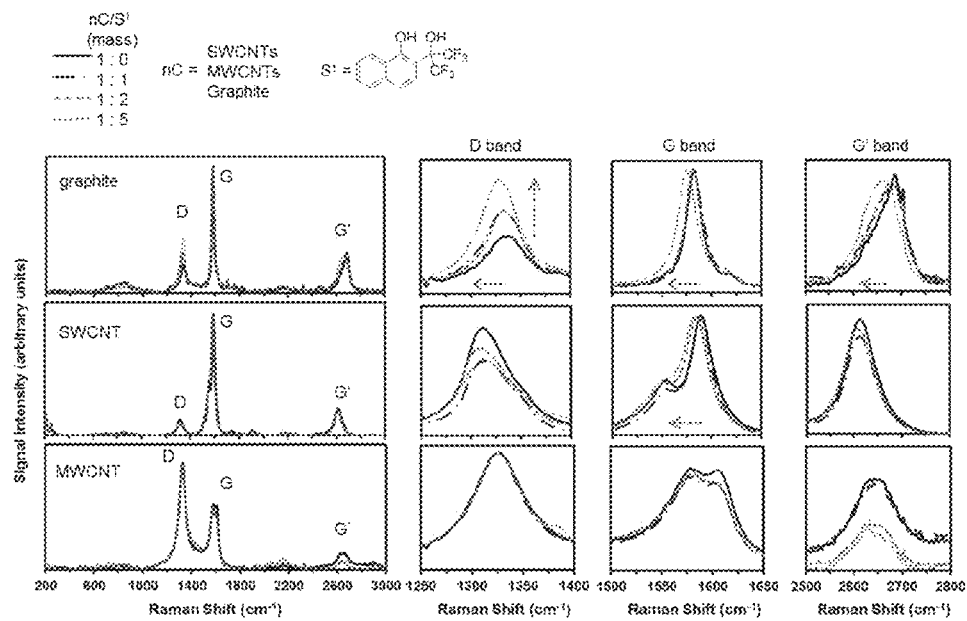
FIG. 11A shows the Raman spectroscopy data for PENCILs (excitation wavelength=632.7 nm) based on different mass ratios of selector 1 (S1) with graphite, SWCNTs, and MWCNTs.
Figure 11B:
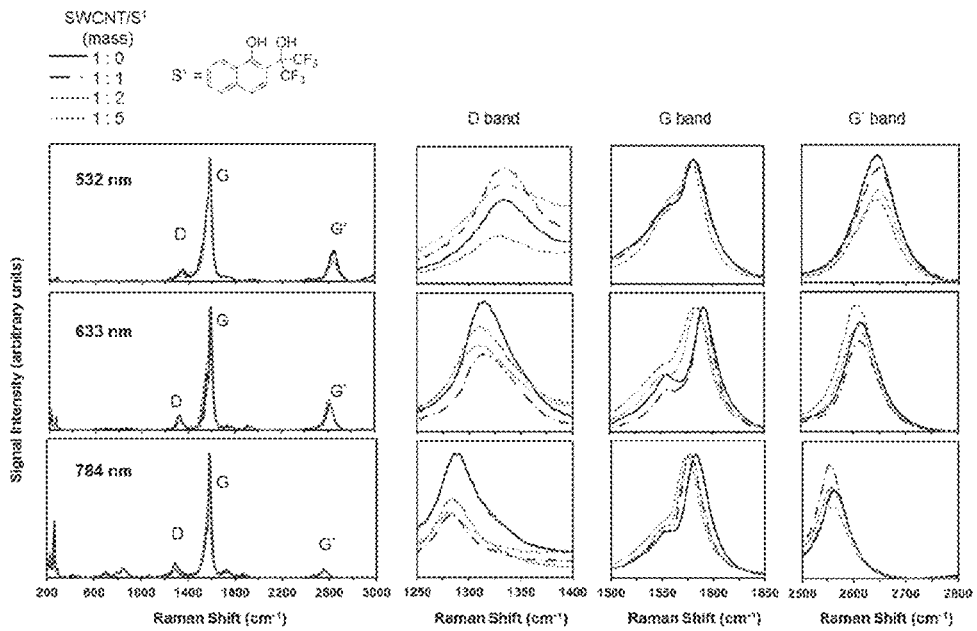
FIG. 11B shows Raman Spectroscopy of SWCNT/selector 1 composites at different excitation wavelengths.

FIG. 11A shows the Raman spectroscopy of PENCILs (excitation wavelength=632.7 nm) based on different mass ratios of selector 1 with graphite, SWCNTs, and MWCNTs, confirming the presence of graphite, SWCNTs, and MWCNTs within the respective composites with no evidence of covalent functionalization of nC with selectors, no indication of exfoliation of graphite into graphene. FIG. 11B shows the Raman spectroscopy of SWCNT/selector 1 composites at three different excitation wavelengths, 532 nm, 633 nm, and 784 nm, revealing no significant systematic changes in the ratio of intensities of D to G bands (ID/IG) with incorporation of selector 1 that would be expected in the case of covalent modification of SWCNTs. In the case of graphite, increasing the concentration of selector 1, [$S^1$], systematically increased the ratio of intensities of D to G bands ($I_D/I_G$). Without wishing to be bound by theory, this increase in $I_D/I_G$ may indicate increased disorder of the $sp^2$ lattice and potential reduction in size of graphite crystallites with increased [$S^1$]. No systematic increase in $I_D/I_G$ was observed for composites of selector 1 with SWCNTs and MWCNTs. (FIG. 11A) Raman spectra of composites of selector 1 with SWCNTs and graphite also showed a small downshift (1-2 $cm^{-1}$) in the positions of D and G bands of these nCs with increasing [$S^1$] within the blend. These downshifts may result from dispersive and doping interactions between selector 1 and nC.

Figure 12A:
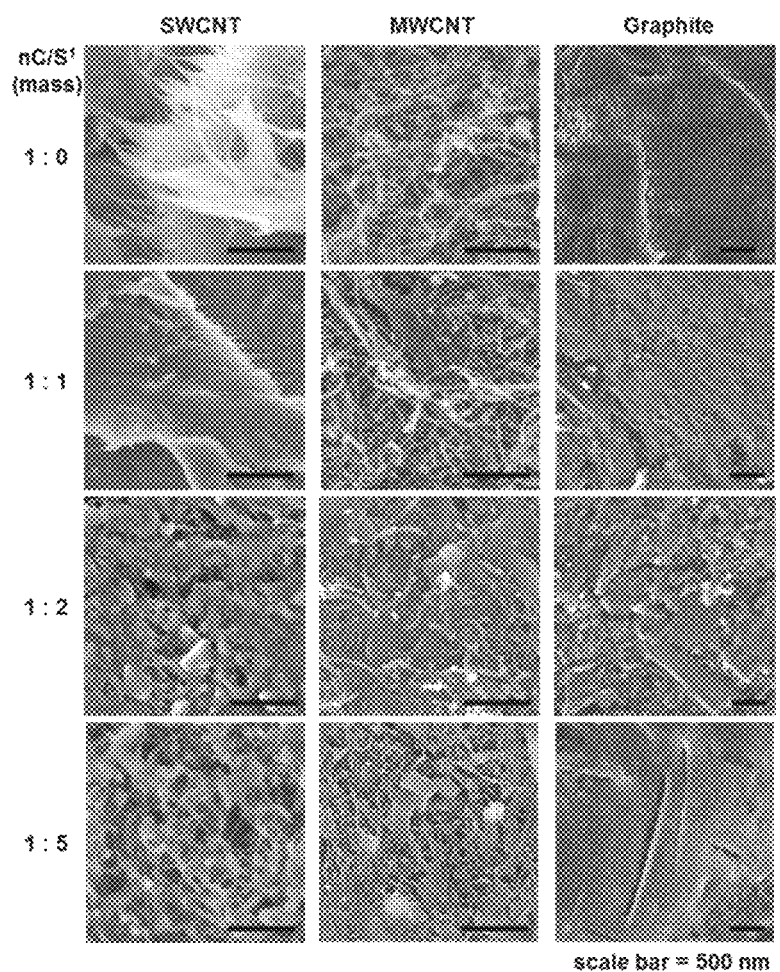
FIG. 12A shows Scanning Electron Microscopy (SEM) images of PENCILs based on selector 1 blended SWCNTs, MWCNTs, and graphite at different mass ratios (nC to selector 1 or S1).
Figure 12B:
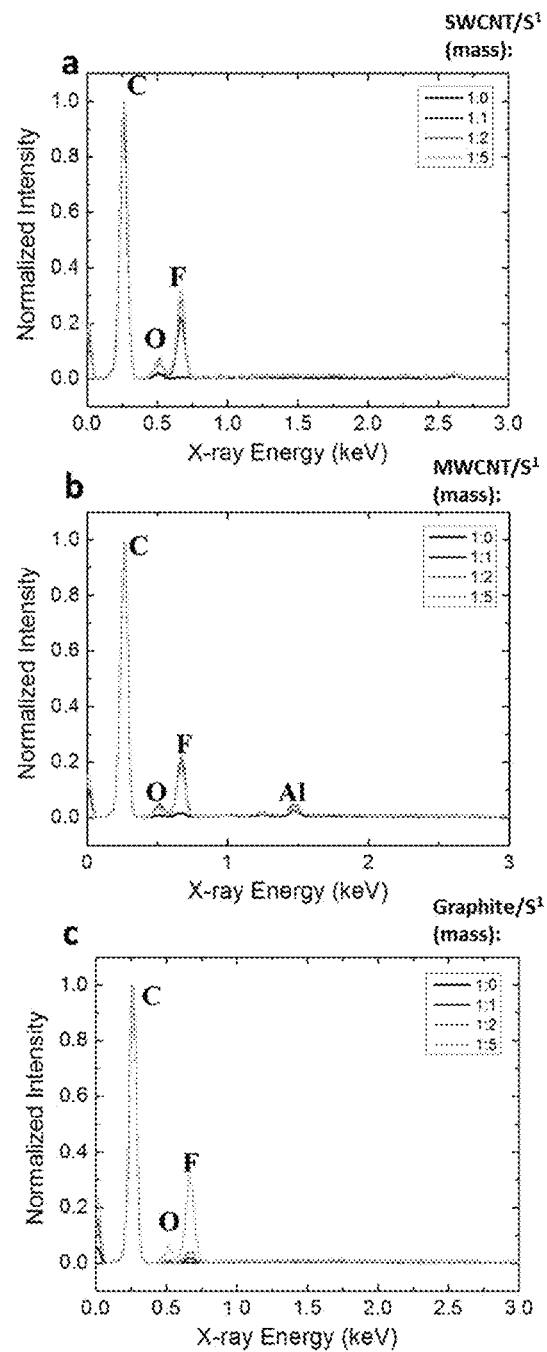
FIG. 12B shows X-ray survey scans of SWCNT/selector 1, MWCNT/selector 1, and graphite/selector 1 composites.
Figure 13:
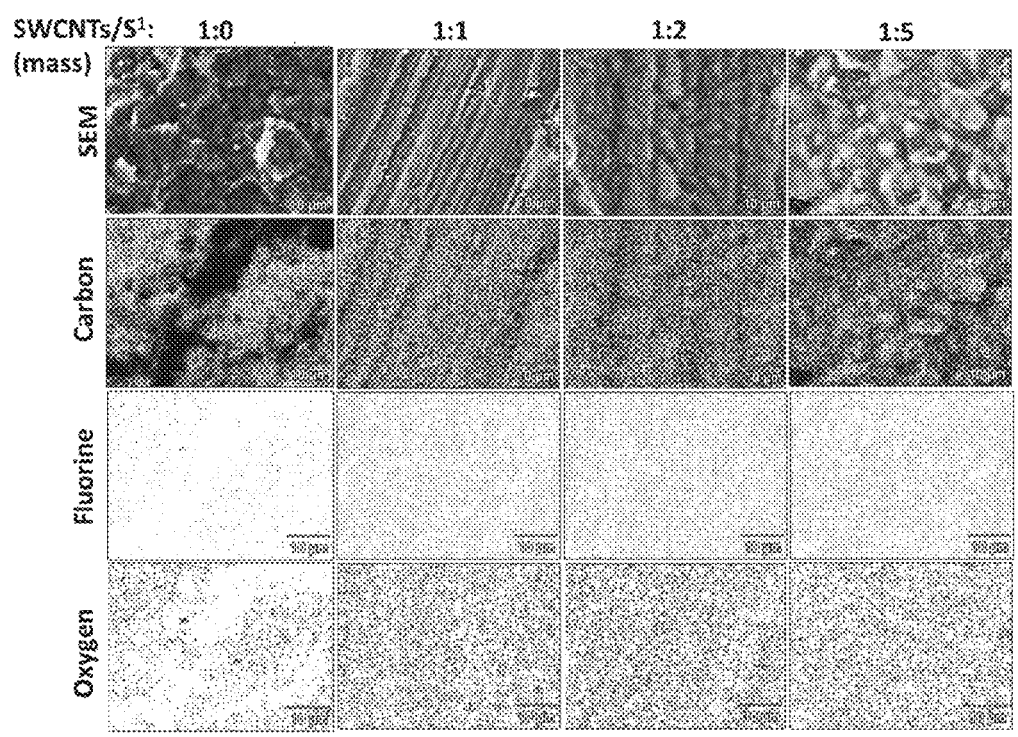
FIG. 13 shows energy-dispersive X-ray spectroscopy (EDX) images of SWCNT/selector 1 composites at different mass ratios.
Figure 14:
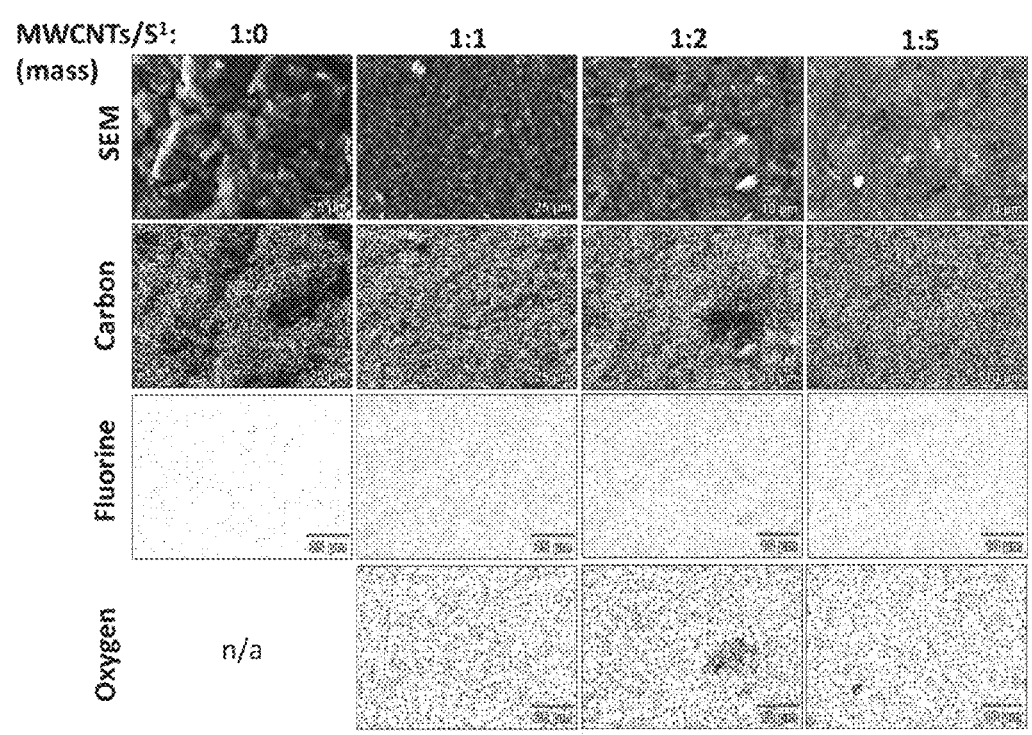
FIG. 14 shows EDX images of MWCNT/selector 1 composites at different mass ratios.
Figure 15:
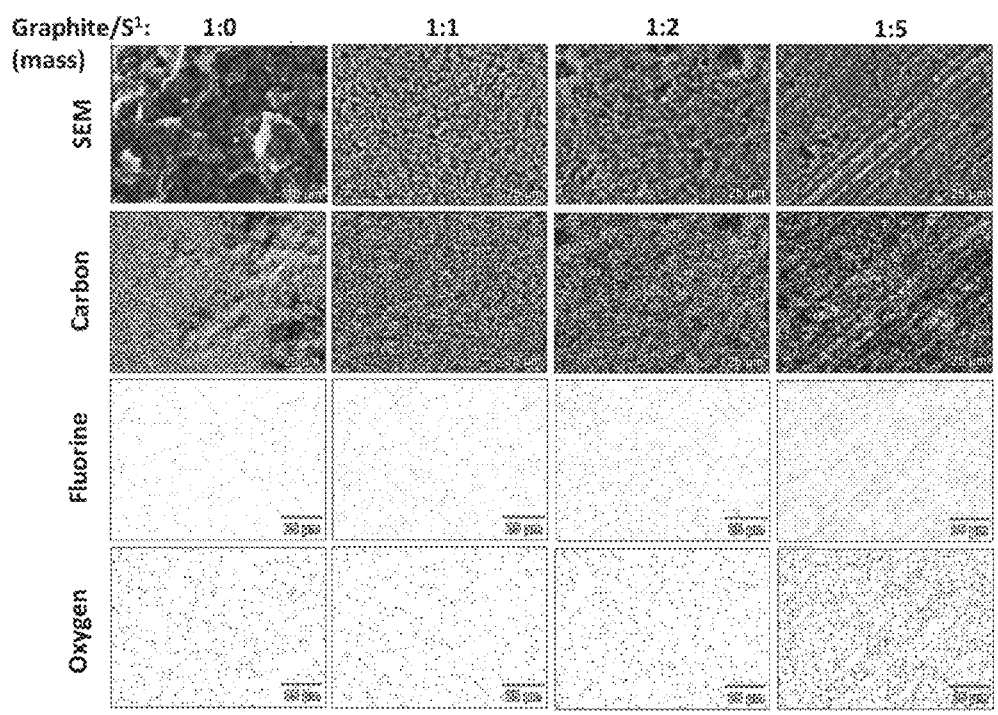
FIG. 15 shows EDX images of graphite/selector 1 composites at different mass ratios.

Further analysis of PENCILs with EDX revealed uniform dispersion of selector 1 and nC within the composite on microscale. (FIG. 12-15) Samples were examined by SEM to obtain information about the nanoscale structure of the composites. FIG. 12 shows high-resolution SEM images of composites of selector 1 with graphite, SWCNTs, and MWCNTs at four different mass ratios (nC/selector 1=1:0, 1:1, 1:2, and 1:5). The presence of selector 1 was shown to alter the nanoscopic structure of composites for all forms of nC by coating the surface of SWCNTs, MWCNTs, and graphite crystallites. The PENCILs were also characterized by conductivity measurements with a 4-point probe and mechanical analysis by nanoindentation. As shown in Table 1, PENCILs exhibited a systematic decrease in bulk conductivity with increasing [$S^1$] (e.g., 256 S/cm for 1:0 SWCNT/selector 1, 56 S/cm for 1:1 SWCNT/selector 1, 25 S/cm for 1:2 SWCNT/selector 1, and 2 S/cm for 1:5 SWCNT/selector 1. This systematic decrease in conductivity (i.e., increase in resistance) may indicate that selector 1 coats the surface of nC and thus increases the barrier for the transfer of electrons between nC-nC junctions. Mechanical analysis by nanoindentation revealed that the PENCILs based on SWCNT/selector 1 and graphite/selector 1 composites have a similar range of hardness (10-500 MPa; Table 2) to those of conventional commercial graphite-based pencil "leads" PENCILs (e.g., 100 MPa for a standard HB pencil). Blending selector 1 with nC reduced the hardness of the resulting composite (e.g., from 118 MPa for 1:0 SWCNT/selector 1 to 7 MPa for 1:5 SWCNT/selector 1). Table 3 shows the bulk conductivity σ of 1:4 nC/S composites used for rapid prototyping of sensing arrays.

TABLE 1

Bulk conductivity σ of nC/$S^1$ composites.

| nC/$S^1$ | σ (S/cm) nC = SWCNTs | σ (S/cm) nC = MWCNTs | σ (S/cm) nC = Graphite |
|---|---|---|---|
| 1:0 | 256 ± 5 | 14.9 ± 0.2 | 884 ± 28 |
| 1:1 | 56 ± 2 | 13.1 ± 0.1 | 82 ± 3 |
| 1:2 | 25 ± 1 | 11.3 + 0.1 | 21.9 ± 0.3 |
| 1:5 | 2.3 ± 0.1 | 3.1 ± 0.1 | 1.4 ± 0.3 |

TABLE 2

Hardness (H) of nC/S[1] composites.

| nC/S[1] | H (MPa)<br>nC = SWCNTs | H (MPa)<br>nC = Graphite |
|---|---|---|
| 1:0 | 118 ± 53 | 478 ± 262 |
| 1:1 | 160 ± 62 | 21 ± 7 |
| 1:2 | 59 ± 34 | 98 ± 57 |
| 1:5 | 7 ± 4 | 176 ± 72 |

TABLE 3

Bulk conductivity σ of 1:4 nC/S composites used for rapid prototyping of sensing arrays.

| Selector (FIG. 10) | σ (S/cm)<br>nC = SWCNTs | σ (S/cm)<br>nC = Graphite |
|---|---|---|
| 1  | 2.2 ± 0.2    | 3.13 ± 0.03 |
| 2  | 17 ± 1       | 35 ± 2      |
| 3  | 8 ± 7        | 0.61 ± 0.07 |
| 4  | 48 ± 7       | 11 ± 2      |
| 5  | 43 ± 8       | 4.0 ± 0.1   |
| 6  | 0.32 ± 0.02  | 0.91 ± 0.04 |
| 7  | 12.5 ± 0.2   | 3.0 ± 0.2   |
| 8  | 8.0 ± 0.3    | 11.5 ± 0.2  |
| 9  | 19 ± 3       | 18.8 ± 0.5  |
| 10 | 28 ± 1       | 3.2 ± 0.1   |
| 11 | 0.20 ± 0.01  | 40 ± 3      |
| 12 | 30 ± 3       | 8.4 ± 0.1   |

Example 10

In the following example, the vapor sensing performance of chemiresistors including nC/selector 1 composites fabricated in Example 9 was evaluated.

Fabrication of Sensors by Deposition of Resistors with Abrasion Fabrication Technique (DRAFT): Sensing materials were deposited on the surface of paper between gold electrodes by manual abrasion of PENCILs at a rate of ~10 mm/s with an applied force of ~1-5 N several times to obtain the desired resistance of devices (typically ~10-50 kΩ). Precise control over the rate of deposition or the applied force was not necessary; we obtained good reproducibility in sensing response between devices examined in this study.

Sensing Measurements: The array of devices was mounted onto a 25 mm×75 mm×1 mm glass slide using a double sided Scotch tape. The array was then inserted into a 2×30 pin edge connector (DigiKey), which made electrical contacts with each of the gold electrodes within the array. The edge connector was then connected to the potentiostat via a breadboard (DigiKey). For sensing measurements, the devices were enclosed within a custom-made gas-tight Teflon chamber containing an inlet and outlet port for gas flow. The inlet port was connected to a gas delivery system, and the outlet port was connected to an exhaust vent. Measurements of conductance were performed under a constant applied voltage of 0.1 V using PalmSense EmStat-MUX equipped with a 16-channel multiplexer (Palm Instruments BV, The Netherlands, http://www.palmsens.com/). Data aquisition was done using PSTrace 2.4 software provided by Palm Instruments. Matlab (R2011a, Mathworks) and Microsoft Excel were used to perform baseline correction, calculate relative sensing responses, and perform principal component analysis.

Dilution of Gases: Delivery of controlled concentration of gases ($NH_3$ and $NO_2$) to devices were performed using Smart-Trak Series 100 (Sierra Instruments, Monterey, Calif.) gas mixing system at total flow rates of 1 L/min $NH_3$ was diluted with $N_2$, and $NO_2$ was diluted with air.

Dilution of Vapors: Delivery of controlled concentrations of vapors to devices was carried out using Precision Gas Standards Generator Model 491M-B (Kin-Tek Laboratories, La Marque, Tex.). All vapors were diluted with $N_2$ at total flow rates of 0.25-0.50 L/min DRAFT of the nC/selector 1 composites between gold electrodes on the surface of weighing paper produced functional devices (typical range of resistance between 10-50 kΩ). Devices including compressed blends of nC (graphite, SWCNTs, MWCNTs) and selector 1 at different mass ratios (1:0, 1:1, 1:2, and 1:5) were fabricated. Sensing performance of the devices was examined by applying a constant voltage (0.1 V) across the gold electrodes and monitoring the change in current upon exposure to the target analytes using a potentiostat. The sensing response $-\Delta G/G_0$(%) was calculated by observing the normalized difference in current before ($I_0$) and after (I) the exposure to the analyte: $-\Delta G/G_0(\%)=[(I_0-I)/I_0]\times 100$. All sensors (each type in triplicate) were exposed to the analytes for 30 s followed by 170 s recovery under a constant flow of nitrogen. The concentrations of analytes for this experiment were chosen to be sufficiently high (~1% of equilibrium vapor pressure at 25° C.) to obtain a measurable response from the pristine forms of nC. Comparing response of pristine nC to nC/selector 1 blends yielded quantitative information about signal enhancement in the presence of selector 1.

Figure 16:
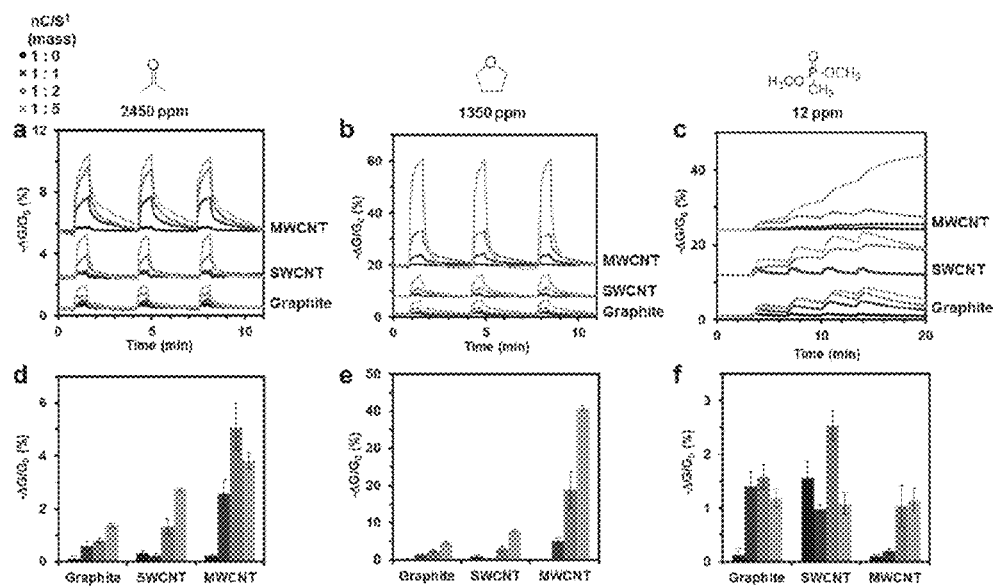
FIG. 16 shows various graphs illustrating the change in conductance of sensors containing different mass ratios of nC/selector 1 upon exposure to (a, d) acetone, (b, e) THF, and (c, f) DMMP, for 30 s.

FIG. 16 shows the response of the sensors toward acetone, THF, and DMMP, including the change in conductance (represented as $-\Delta G/G_0$, %) with time upon exposure to acetone (FIG. 16A), THF (FIG. 16B), and DMMP (FIG. 16C) for 30 s. Quantitative comparison of the sensing response ($-\Delta G/G_0$, %) toward acetone (FIG. 16D), THF (FIG. 16E), and DMMP (FIG. 16F) for three different forms of nC (graphite, SWCNT, MWCNT) blended with selector 1 at four different mass ratios (1:0, 1:1, 1:2, and 1:5) is also shown. Vertical error bars represent standard deviation from the mean based on three exposures of three sensors to each of the analytes.

As shown in FIG. 16, blending selector 1 with nC enhanced response toward target analytes by up to 1-2 orders of magnitude for various forms of nC. For instance, when 1:5 MWCNT/selector 1, SWCNTs/selector 1, graphite/selector 1 are exposed to THF vapor, a 164-fold, 8-fold, and 14-fold enhancement in sensing response, respectively, was observed, compared to the corresponding forms of nC in the absence of selector 1. (FIG. 16) This enhancement in the sensing response may be attributed in part to the favorable adsorption of the analytes to the selector 1-coated surface of the nC, and the ability of nC/selector 1 composites to transduce this molecular interaction as a change in electrical properties. The magnitude and reversibility of the sensing response of nC/selector 1 composites toward specific analytes may be a complex function of at least three experimental parameters: i) the type of analyte; ii) the type of nC; and iii) nC/selector 1 ratio. (FIG. 16) Due to their differences in chemical structure, each of the analytes in this example has a unique set of kinetic and thermodynamic constants that drive its molecular association and dissociation with the selector 1-coated surface of nC. Comparing left, middle, and right-hand panels of FIG. 16 reveals how the type of analyte (acetone vs. THF vs. DMMP) can influence the sensing response of devices. For example, the sensors exhibit a reversible response toward acetone and THF (FIGS. 16A-B), and only a partially reversible response toward DMMP on the time scale of the experiment (FIG. 16C). Such differences in reversibility may be due, at least in part, to differences in the kinetic and thermodynamic parameters that characterize the interaction of the analytes with the selector 1-coated surface of each nC.

FIG. 16 also yields information about how the type of nC (graphite vs. SWCNTs vs. MWCNTs) and the nC/selector 1 ratio influences the sensing response of devices. In general, systematically increasing [$S^1$] within the composites increased the sensing response of the corresponding devices toward acetone and THF. (FIG. 16A-B, D-E) By contrast, the enhancement in sensing response of the devices toward DMMP exhibited a less systematic dependence on [$S^1$] within the blend. (FIG. 16F)

Interestingly, the magnitude of the sensing response of graphite/selector 1 composites toward DMMP was comparable to those based on much more expensive forms of carbon, such as SWCNT/selector 1 and MWCNT/selector 1. (FIG. 16F) The dependence of sensing response on the type of nC can be attributed in part to the differences in: i) the surface-to-volume ratio of individual particles of nC, ii) the length and the number of available conduction pathways within the composite, and iii) the efficiency of mixing between selector 1 and nC within the composite. Thus, nC/selector within the composite (at least 1:2 or 1:5 by mass in the case of nC/selector 1) can be an important parameter for maximizing the response of the sensors toward target analytes.

Example 11

Figure 22:
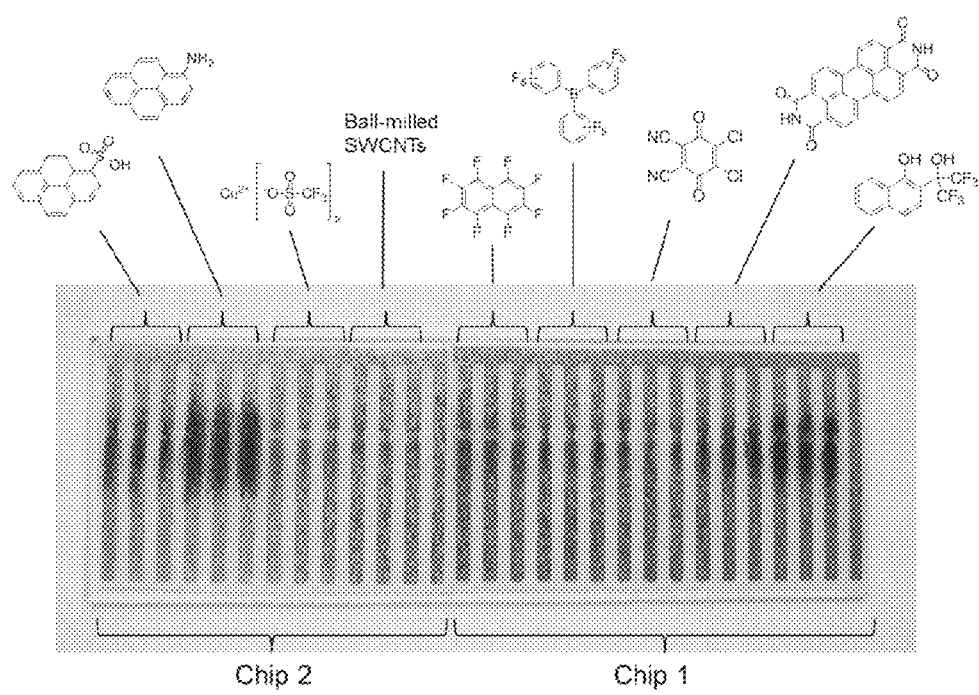
FIG. 22 shows a photograph of selected sensors from a SWCNT-based array.

The following example describes the rapid prototyping of selective sensors within cross-reactive arrays. To demonstrate the generality of the process for fabricating selective gas and vapor sensors from PENCILs by DRAFT, an array of cross-reactive sensors was constructed. FIG. 22 shows a photograph of the array, where each sensor was drawn in triplicate on the surface of weighing paper chip between gold electrodes. The typical resistance range of the sensors was observed to be 10-50 k$\Omega$. FIG. 22 shows two weighing paper chips mounted on the surface of a glass slide using double sided tape. This arrayed format is modular, straightforward to implement, and can facilitate evaluation of sensing performance of multiple devices simultaneously. Each sensor within the array included a ball milled and compressed solid composite of SWCNTs with a specific selector (1:4 SWCNT:selector by mass) deposited on the surface of weighing paper by DRAFT; an additional sensor based on pristine ball-milled SWCNTs served as a control for evaluating enhancements in sensitivity and selectivity of the SWCNT/S composites toward specific analytes.

Figure 17:
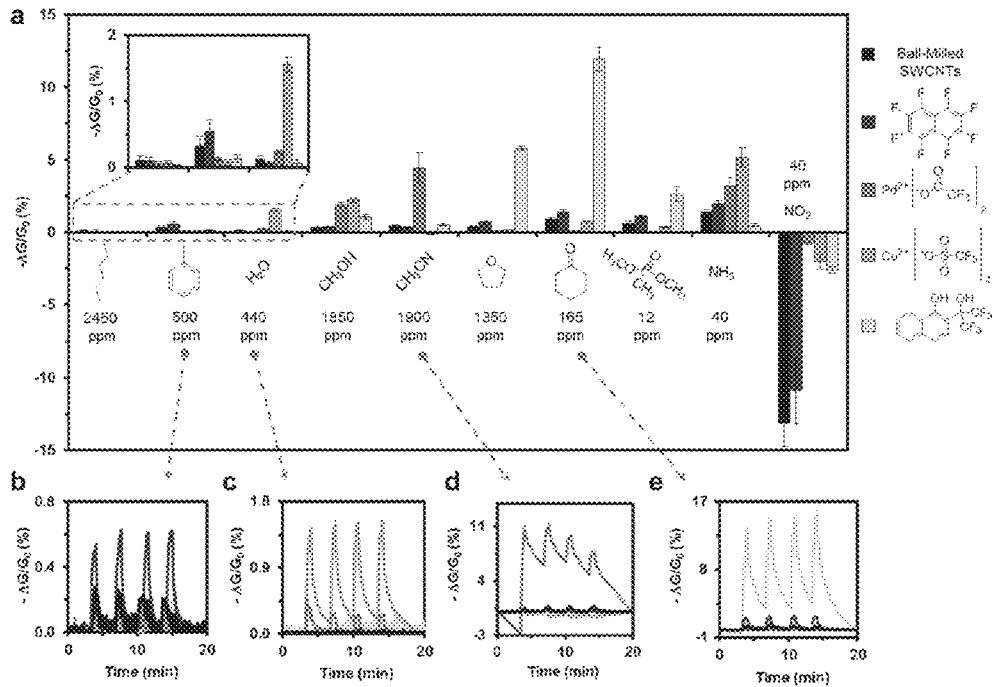
FIG. 17 shows a graph summarizing the change in conductance of five chemically distinct sensors toward ten different analytes, (a) from exposure of the sensors to eight vapors and two gases (40 ppm each), (b) from exposure of the device including selector 2 towards toluene, (c) from exposure of the device including selector 3 towards water vapor, (d) from exposure of the device including selector 4 towards acetonitrile, and (e) from exposure of the device including selector 1 towards cyclohexanone.

FIG. 17 summarizes the magnitude of the sensing response of the five chemically distinct sensors toward ten different analytes. FIG. 17A shows the change in conductance (represented as $-\Delta G/G_0$, %) resulting from exposure of the array to eight vapors (at ~1% equilibrium vapor pressure, specific concentrations as shown) and two gases (40 ppm each). Each bar represents the average response of three sensors exposed to each analyte in triplicate. FIG. 17B shows the signal exhibited by the device including selector 2 towards toluene; FIG. 17C shows the signal exhibited by the device including selector 3 towards water vapor; FIG. 17D shows the signal exhibited by the device including selector 4 towards acetonitrile; and FIG. 17E shows the signal exhibited by the device including selector 1 towards cyclohexanone.

Each sensing response represents the average change in conductance $-\Delta G/G_0$(%) from three devices fabricated using the same PENCIL and simultaneously exposed to each analyte at least 3 times (9 total measurements). Compared to SWCNT control, incorporation of selectors 1-4 into SWCNT composites produced devices with enhanced selectivity and sensitivity towards selected analytes. For instance, incorporation of selector 1 (an H-bond donor) enhanced sensitivity toward H-bond acceptors (e.g., 15× for THF, 13× for cyclohexanone, and 4× for DMMP), incorporation of selector 2 enhanced sensitivity toward electron-rich aromatics (e.g., 2× for toluene), incorporation of selector 3 (a Lewis acid) showed enhanced sensitivity toward Lewis bases (e.g., 12× for $H_2O$, 7× for $CH_3OH$, and 4× for $NH_3$,), while sensors containing selector 4 enhanced sensitivity towards $CH_3OH$ (6×) and $CH_3CN$ (9×).

Figure 18:
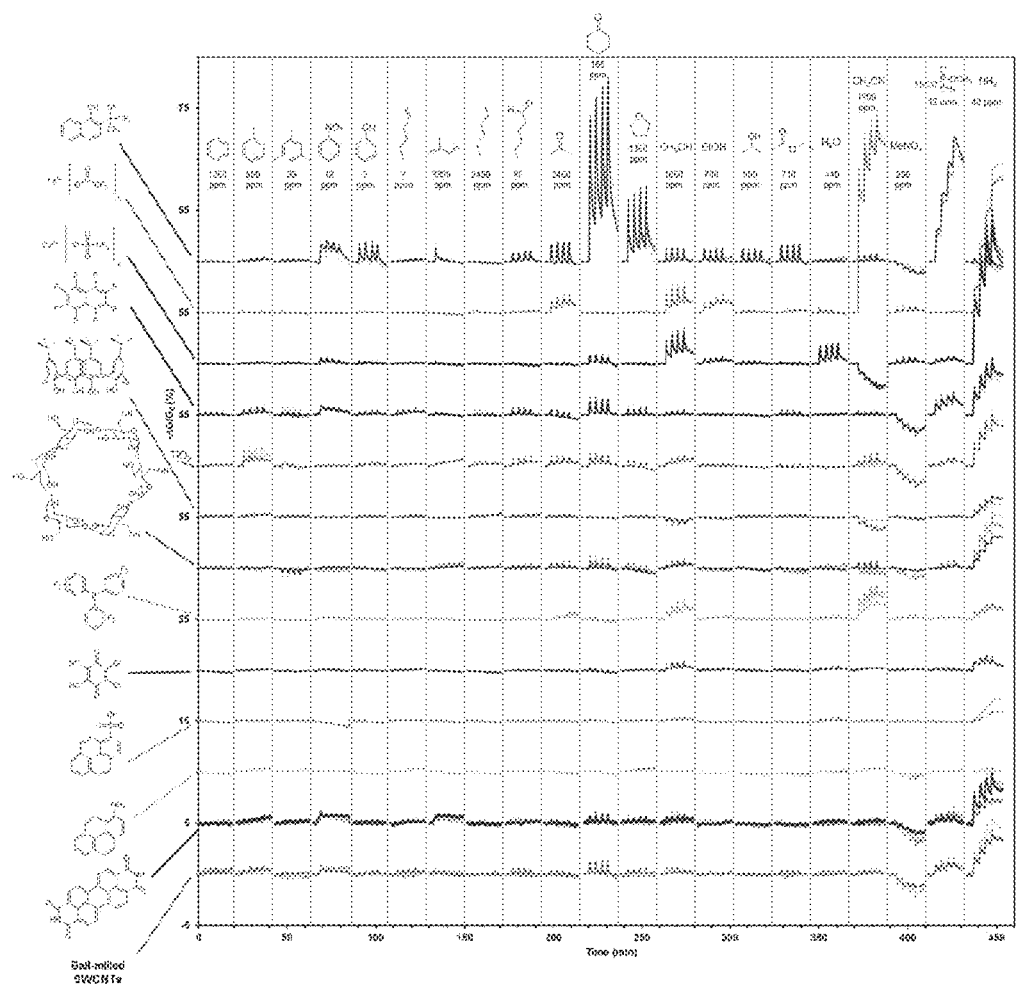
FIG. 18 show a graph of the sensing responses ($-\Delta G/G_0$, %) with time of SWCNT-based arrays towards various analytes, with no baseline correction.
Figure 19:
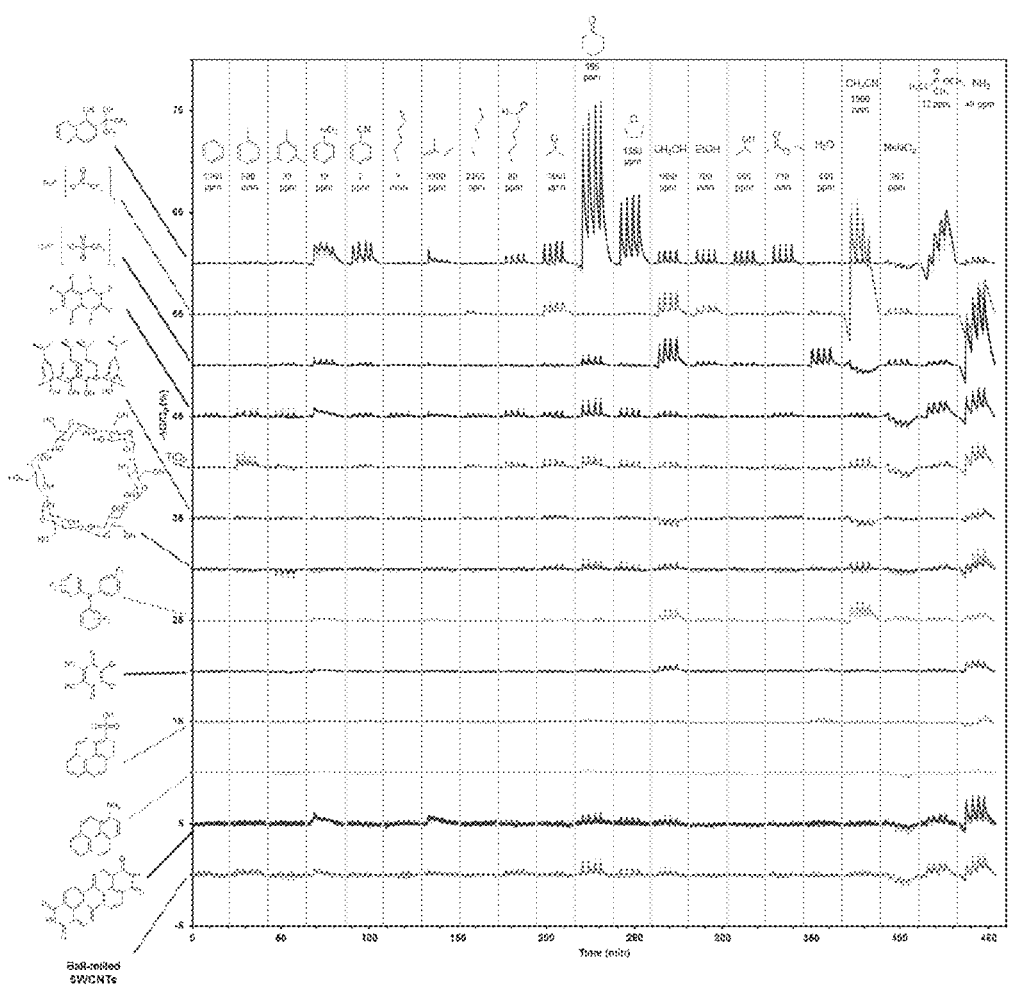
FIG. 19 show a graph of the sensing responses ($-\Delta G/G_0$, %) with time of SWCNT-based arrays towards various analytes, with linear baseline correction.
Figure 23:
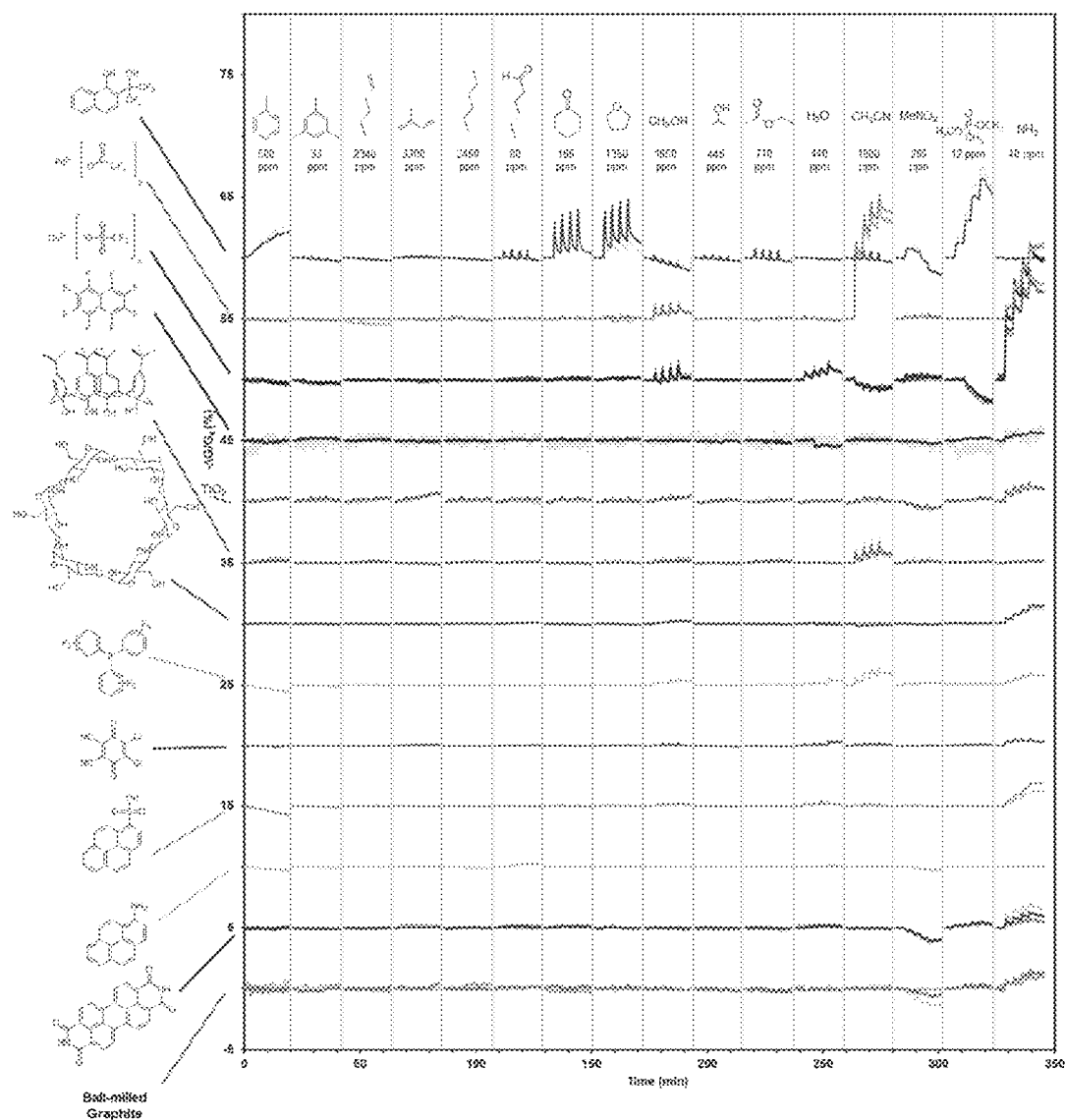
FIG. 23 shows the sensing response ($-\Delta G/G_0$, %) with time of graphite-based array towards various analytes, with no baseline correction.
Figure 24:
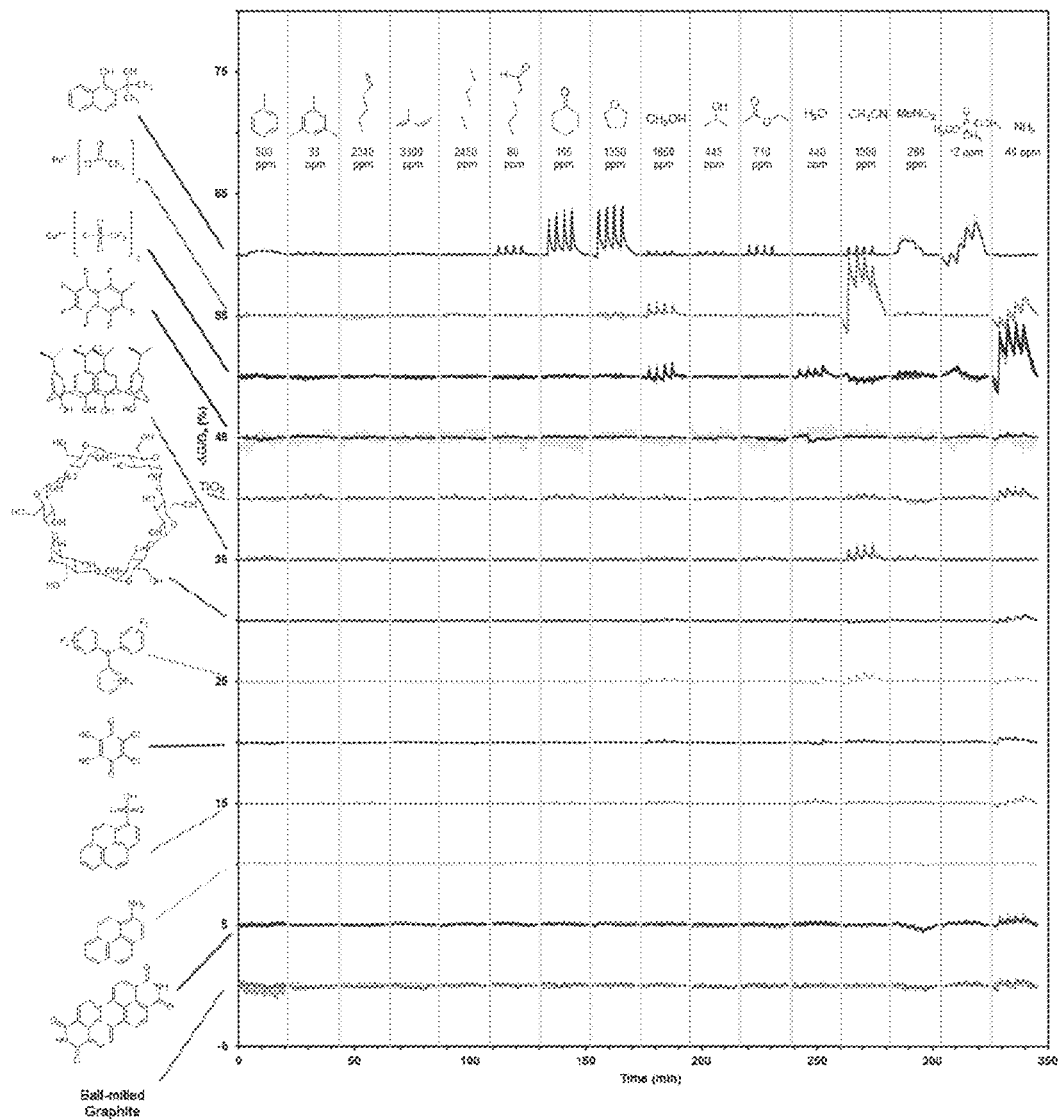
FIG. 24 shows the sensing response ($-\Delta G/G_0$, %) with time of graphite-based array towards various analytes, with linear baseline correction.

Additional selectors were also examined in this example. The sensing response ($-\Delta G/G_0$, %) with time of SWCNT-based array towards various analytes is shown in FIG. 18, with no baseline correction, and in FIG. 19, with linear baseline correction. Each type of sensor was examined in triplicate; the multiple sensing responses for each selector are overlayed to show reproducibility. Compared to pristine SWCNTs, composites of these selectors with SWCNTs showed increased selectivity, but no large enhancements in sensitivity compared to unmodified SWCNTs toward target analytes. To probe the generality of this method for various forms of nC, an array of cross-reactive sensors from graphite-based composites with selectors 1-12 (1:4 graphite/S by mass) were constructed. FIG. 23 shows the sensing response ($-\Delta G/G_0$, %) with time of graphite-based array towards various analytes (no baseline correction was applied to the sensing responses; each type of sensor was examined in triplicate; and multiple sensing responses for each type of sensor are overlayed to show reproducibility). FIG. 24 shows the sensing response ($-\Delta G/G_0$, %) with time of graphite-based array towards various analytes (linear baseline correction was applied to all sensing responses; each type of sensor was examined in triplicate; multiple sensing responses for each type of sensor are overlayed to show reproducibility).

Figure 25:
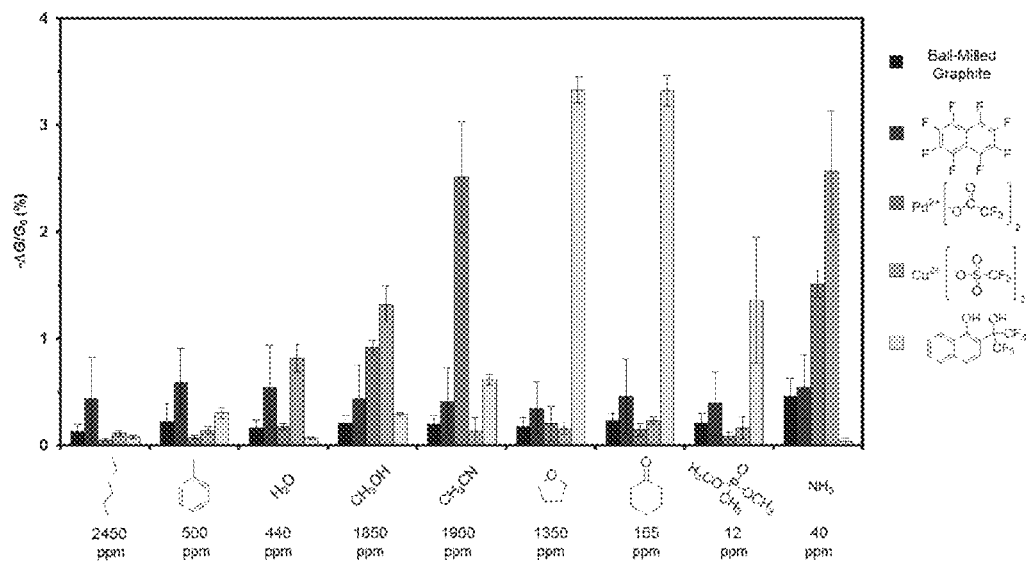
FIG. 25 shows a bar graph illustrating the sensing response of a cross-reactive array including compressed graphite, or composites of graphite with selectors 1-4 (1:4 nC/S by mass), to a variety of analytes.

FIG. 25 summarizes the quantitative sensing response for selected devices and analytes, showing the sensing response of a cross-reactive array fabricated by mechanical abrasion of ball milled and compressed graphite and composites of graphite with selectors 1-4 with (1:4 nC/S by mass) on the surface of weighing paper. The change in conductance (represented as $-\Delta G/G_0$, %) resulting from exposure of the array to eight vapors (at ~1% equilibrium vapor pressure, specific concentrations as shown) and $NH_3$ gas (40 ppm) is shown in FIG. 25, with each bar representing the average response of three sensors exposed to each analyte in triplicate. Vertical error bars represent the standard deviation from the average.

Figure 20:
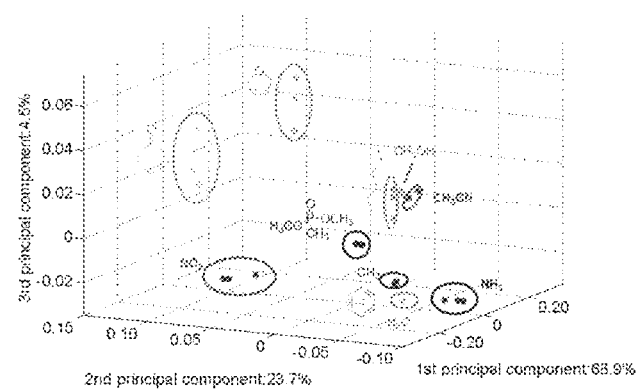
FIG. 20 shows the principal component analysis (PCA) of cross-reactive array shown in FIG. 17.
Figure 21A:
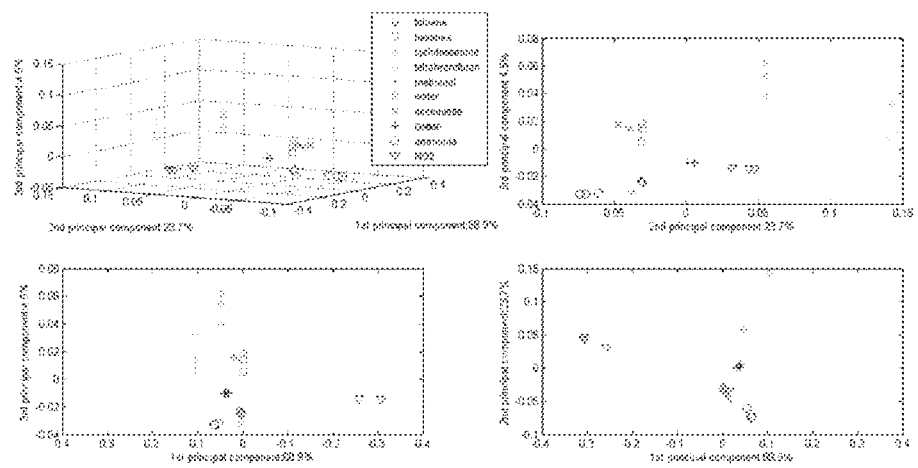
FIG. 21A shows the PCA of SWCNT-based array with 3D and 2D projections of principal components.
Figure 21B:
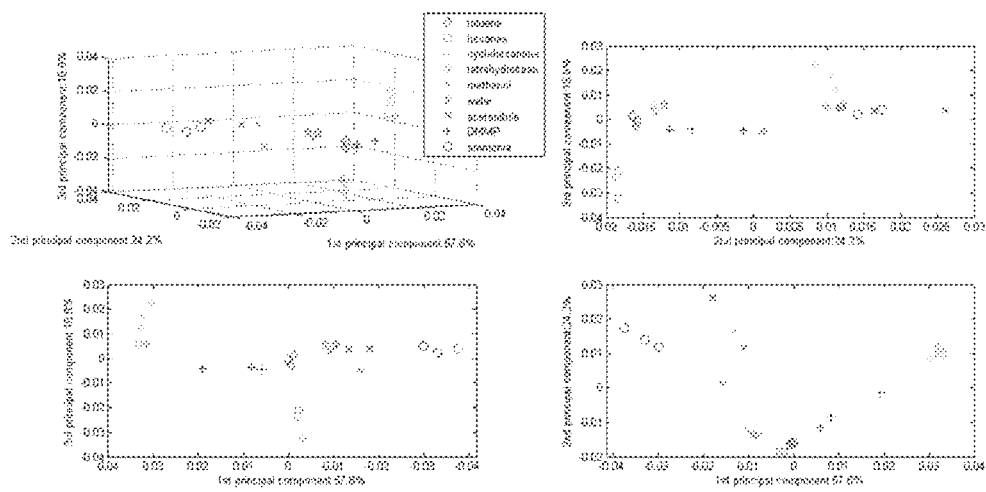
FIG. 21B shows the PCA of the sensing response of a graphite-based sensor array toward nine selected analytes with 3D and 2D projections of principal components.
Figure 21C:
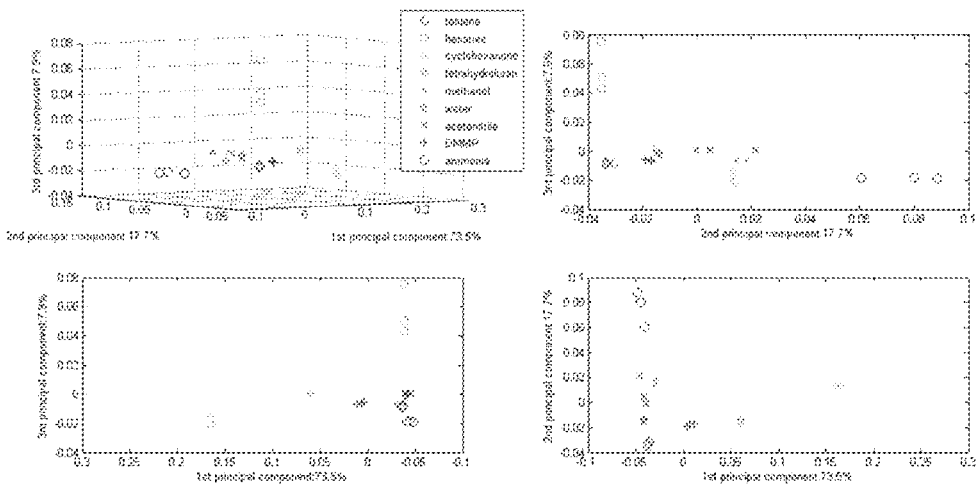
FIG. 21C shows the PCA of the response of SWCNT-based sensor array toward nine selected analytes with 3D and 2D projections of principal components.
Figure 26:
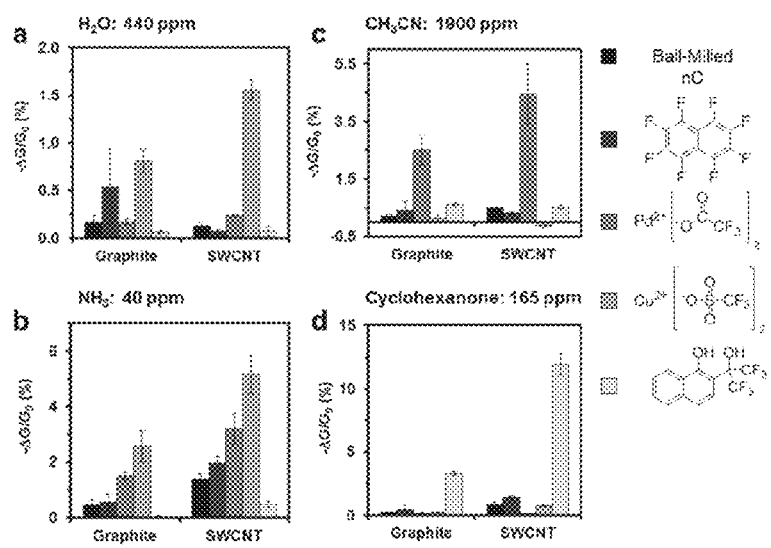
FIG. 26 shows bar graphs of the sensing response ($-\Delta G/G_0$, %) of sensors including compressed blends of graphite or SWCNTs with selectors 1-4 (1:4) by mass toward (a) water, (b) ammonia, (c) acetonitrile, and (d) cyclohexanone.

FIG. 26 shows the quantitative comparison of sensing response ($-\Delta G/G_0$, %) toward water (a), ammonia (b), acetonitrile (c), and cyclohexanone (d) of sensors fabricated on the surface of weighing paper by mechanical abrasion of PENCILs comprising compressed blends of graphite and SWCNTs with selectors 1-4 (1:4) by mass. Vertical error bars represent standard deviation from the mean based on three exposures of three sensors to each of the analytes. Analogous to the SWCNT-based array, blending of selectors 1, 3, and 4 with graphite produced sensing materials and devices with enhanced selectivity and sensitivity towards selected analytes. Notably, these graphite-based sensing materials showed enhanced selectivity and sensitivity towards target analytes in comparison to both graphite and SWCNT controls. (FIG. 26) Although SWCNT-based composites with selectors 1-4 exhibited higher sensing response towards the target analytes compared to their graphite-based analogs, the results summarized in FIG. 26 suggest that inexpensive forms of carbon, such as graphite, can be readily used for solvent-free rapid prototyping and identification of selective chemiresistive sensing materials based on binary mixtures of selectors and nC. Once these selective materials have been identified, optimization of the source of nC can yield materials and devices with enhanced chemical properties for specific applications. To evaluate the ability of the sensor arrays fabricated on paper from PENCILs by DRAFT to identify and discriminate different gases and VOCs, the sensing results were examined using principal component analysis (PCA). FIG. 20 shows the ability of the five-sensor SWCNT-based array presented in FIG. 17 to resolve ten chemically diverse analytes using the first three principal components (PCs). FIG. 21A illustrates resolution of analytes using 2D projections of PCs. FIGS. 21B-C show the analogous capability of the graphite-based and SWCNT-based arrays based on composites with selectors 1-4 to resolve nine different analytes using the first three PCs of each array.

In summary, a simple and versatile method for fabricating selective chemiresistive sensors from graphitic materials on the surface of paper has been developed. A new class of sensing materials that includes solid composites of small molecule selectors with nanostructured carbon (nC, i.e., graphite, SWCNTs, MWCNTs) generated by mechanical mixing and subsequent compression has been studies. These sensing materials can be designed and produced from many different forms of nC, and can be easily integrated into functional chemiresistive gas sensors and cross-reactive arrays by mechanical abrasion on the surface of paper.

What is claimed:

1. A method for fabricating a device, comprising:
arranging a plurality of devices to form an array, wherein each individual device includes a species responsive to an analyte, such that a first device includes a species responsive to a first analyte and a second device includes a species responsive to a second analyte, the first and second analytes being different, wherein each individual device is formed by:
providing an article comprising a conductive material, wherein the conductive material comprises nanostructures;
contacting the article with a surface of a substrate, a first electrode, and a second electrode via mechanical abrasion, thereby forming the conductive material on the surface of the substrate, the first electrode, and the second electrode, and forming an electrical circuit comprising the conductive material.

2. A method as in claim 1, wherein the article is contacted in the absence of a solvent.

3. A method for fabricating a device, comprising:
providing an article comprising a conductive material, wherein the conductive material comprises nanostructures;
contacting the article with a surface of a substrate, a first electrode, and a second electrode via mechanical abrasion, thereby forming the conductive material on the surface of the substrate, the first electrode, and the second electrode and forming an electrical circuit comprising the conductive material;
applying a potential to the first electrode and the second electrode; and
arranging a species responsive to an analyte and/or to a change in a set of conditions in electrochemical communication with the conductive material on the surface of the substrate such that, in the presence of the analyte or upon occurrence of the change in the set of conditions, a change in a determinable signal of the device is produced.

4. A method as in claim 3, wherein the article further comprises nanostructures, polymers, small molecules, metal-containing species, biological species, or combinations thereof.

5. A method as in claim 3, wherein the article further comprises carbon nanotubes, graphene, polymers, small molecules, metal salts, proteins, DNA, or combinations thereof.

6. A method as in claim 3, wherein the article is in the form of a compressed powder.

7. A method as in claim 3, wherein the substrate is paper, fabric, a polymer, glass, metal, or skin.

8. A method as in claim 3, wherein the species interacts with an analyte to produce the determinable signal.

9. A method as in claim 8, wherein the interaction comprises covalent bonding.

10. A method as in claim 8, wherein the interaction comprises non-covalent bonding.

11. A method as in claim 3, wherein the species is responsive to a change in temperature.

12. A method as in claim 3, wherein the analyte is a chemical species.

13. A method as in claim 3, wherein the analyte is a vapor phase analyte.

14. A method as in claim 3, wherein the analyte is radiation.

15. A method as in claim 3, wherein the device is a sensor, a circuit, a tag for remotely-monitored sensors, a label or tracker for a subject or object, a capacitor, a photovoltaic device, a resistor, a fuse, a transistor, or an antenna.

16. A method as in claim 3, wherein the article is contacted in the absence of a solvent.

17. A method for fabricating a device, comprising:
providing an article comprising a conductive material, wherein the conductive material comprises nanostructures;
contacting the article with a surface of a substrate, a first electrode, and a second electrode via mechanical abrasion, thereby forming the conductive material on the surface of the substrate and forming an electrical circuit comprising the conductive material;
applying a potential to the first electrode and the second electrode, wherein the article further comprises a species responsive to an analyte and/or to a change in a set of conditions, such that contacting the article with the surface of a substrate via mechanical abrasion results in the formation of the conductive material and the species on the surface of the substrate, and such that, in the presence of the analyte or upon occurrence of the change in the set of conditions, a change in a determinable signal of the device is produced.

18. A method as in claim 17, wherein the article further comprises nanostructures, polymers, small molecules, metal-containing species, biological species, or combinations thereof.

19. A method as in claim 17, wherein the article further comprises carbon nanotubes, graphene, polymers, small molecules, metal salts, proteins, DNA, or combinations thereof.

20. A method as in claim 17, wherein the article is in the form of a compressed powder.

21. A method as in claim 17, wherein the substrate is paper, fabric, a polymer, glass, metal, or skin.

22. A method as in claim 17, wherein the species interacts with an analyte to produce the determinable signal.

23. A method as in claim 22, wherein the interaction comprises covalent bonding.

24. A method as in claim 22, wherein the interaction comprises non-covalent bonding.

25. A method as in claim 17, wherein the species is responsive to a change in temperature.

26. A method as in claim 17, wherein the analyte is a chemical species.

27. A method as in claim 17, wherein the analyte is a vapor phase analyte.

28. A method as in claim 17, wherein the analyte is radiation.

29. A method as in claim 17, wherein the device is a sensor, a circuit, a tag for remotely-monitored sensors, a label or tracker for a subject or object, a capacitor, a photovoltaic device, a resistor, a fuse, a transistor, or an antenna.

30. A method as in claim 17, wherein the article is contacted in the absence of a solvent.

* * * * *